US012805841B2

(12) United States Patent
Brem et al.

(10) Patent No.: US 12,805,841 B2
(45) Date of Patent: Nov. 24, 2026

(54) ULTRASOUND SYSTEMS AND METHODS FOR LOCATION-BASED MEDICAL ILLUMINATION OF A REGION OF INTEREST WITHIN A DIMINISHED FIELD OF VIEW

(71) Applicant: BIOSENSE WEBSTER (ISRAEL) LTD., Yokneam (IL)

(72) Inventors: Erez Henri Brem, Yesud Hamaala (IL); Nadav Barnea, Haifa (IL); Guy Haiman, Haifa (IL); Morris Ziv-Ari, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 41 days.

(21) Appl. No.: 18/596,851

(22) Filed: Mar. 6, 2024

(65) Prior Publication Data

US 2025/0281158 A1 Sep. 11, 2025

(51) Int. Cl.
*A61B 8/00* (2006.01)
*A61B 8/08* (2006.01)
(Continued)

(52) U.S. Cl.
CPC ............ *A61B 8/483* (2013.01); *A61B 8/0833* (2013.01); *A61B 8/12* (2013.01); *A61B 8/4254* (2013.01);
(Continued)

(58) Field of Classification Search
None
See application file for complete search history.

(56) References Cited

U.S. PATENT DOCUMENTS 6,049,622 A 4/2000 Robb et al.
6,203,497 B1 3/2001 Dekel et al.
(Continued)

FOREIGN PATENT DOCUMENTS

EP 4179978 A1 * 5/2023 ............... A61B 8/54
WO 9605768 A1 2/1996
(Continued)

OTHER PUBLICATIONS

Wildes, D. et al., "4D ICE: a 2D Array Transducer With Integrated ASIC in a 10-Fr Catheter for Real-Time 3D Intracardiac Echocardiography," in IEEE Transactions on Ultrasonics, Ferroelectrics, and Frequency Control, vol. 63, No. 12, pp. 2159-2173, Dec. 2016, doi: 0.1109/TUFFC.2016.2615602.
(Continued)

*Primary Examiner* — Keith M Raymond
*Assistant Examiner* — Ashish S. Jasani
(74) *Attorney, Agent, or Firm* — Smith, Gambrell & Russell LLP

(57) ABSTRACT

Systems and methods of location-based medical rendering that automatically generate improved renderings, such as 4D ICE imagery, of anatomical structures are disclosed. According to some embodiments methods include: obtaining images and position data from a catheter having a distal tip furnished with an ultrasound imaging device and a position sensor, process the position data of the ultrasound imaging device to determine a volumetric field of regard (FOR) of the imaging device in a patient's body; obtaining a model of at least a portion of a body anatomy present within the FOR; and utilizing the model to optionally: (i) adjust capturing parameters of the ultrasound imaging device based on the model to optimize capturing of a body anatomy of interest by the ultrasound imaging device with diminished appearance of its surrounding tissues; and/or (ii) crop images
(Continued)

grabbed from the FOR of the imaging device to the body anatomy of interest.

24 Claims, 8 Drawing Sheets

(51) Int. Cl.

| | |
|---|---|
| ***A61B 8/12*** | (2006.01) |
| ***G06T 7/11*** | (2017.01) |
| ***G06T 15/08*** | (2011.01) |
| ***G06T 17/00*** | (2006.01) |
| ***G06V 10/25*** | (2022.01) |
| ***G06V 20/50*** | (2022.01) |

(52) U.S. Cl.

CPC ............ *A61B 8/469* (2013.01); *A61B 8/5207* (2013.01); *A61B 8/5223* (2013.01); *A61B 8/54* (2013.01); *G06T 7/11* (2017.01); *G06T 15/08* (2013.01); *G06T 17/00* (2013.01); *G06V 10/25* (2022.01); *G06V 20/50* (2022.01); *A61B 8/0883* (2013.01); *G06T 2200/24* (2013.01); *G06T 2207/10132* (2013.01); *G06T 2207/20132* (2013.01); *G06T 2207/30048* (2013.01); *G06T 2210/41* (2013.01); *G06T 2210/56* (2013.01); *G06V 2201/031* (2022.01)

(56) References Cited

U.S. PATENT DOCUMENTS

| | | | | |
|---|---|---|---|---|
| 6,332,089 | B1 | 12/2001 | Acker et al. | |
| 6,556,695 | B1 | 4/2003 | Packer et al. | |
| 6,618,612 | B1 | 9/2003 | Acker et al. | |
| 6,690,963 | B2 | 2/2004 | Ben-Haim et al. | |
| 6,716,166 | B2 | 4/2004 | Govari | |
| 6,773,402 | B2 | 8/2004 | Govari et al. | |
| 7,020,512 | B2 | 3/2006 | Ritter et al. | |
| 7,536,218 | B2 | 5/2009 | Govari et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 8,456,182 | B2 | 6/2013 | Bar-Tal et al. | |
| 8,696,549 | B2 | 4/2014 | Holsing et al. | |
| 9,392,995 | B2 | 7/2016 | Perrey et al. | |
| 9,980,786 | B2 | 5/2018 | Saul et al. | |
| 10,299,753 | B2 | 5/2019 | Govari et al. | |
| 10,537,306 | B2 | 1/2020 | Schaer et al. | |
| 2002/0065455 | A1 | 5/2002 | Ben-Haim et al. | |
| 2003/0120150 | A1 | 6/2003 | Govari | |
| 2004/0068178 | A1 | 4/2004 | Govari | |
| 2009/0143677 | A1 | 6/2009 | Govari et al. | |
| 2014/0187948 | A1 | 7/2014 | Gerard et al. | |
| 2015/0164605 | A1 | 6/2015 | Patwardhan et al. | |
| 2020/0006134 | A1 | 1/2020 | Dadvand et al. | |
| 2020/0060660 | A1* | 2/2020 | Waechter-Stehle ...... | A61B 8/12 |
| 2022/0168050 | A1* | 6/2022 | Sowards .............. | A61B 8/4472 |
| 2022/0273263 | A1 | 9/2022 | Li et al. | |
| 2022/0409167 | A1 | 12/2022 | Altmann et al. | |
| 2024/0024037 | A1 | 1/2024 | Matsumura et al. | |
| 2024/0268792 | A1* | 8/2024 | Lu ........................ | A61B 8/5223 |
| 2024/0404066 | A1* | 12/2024 | Weber ........................ | G06T 7/11 |

FOREIGN PATENT DOCUMENTS

| | | | | |
|---|---|---|---|---|
| WO | WO2008/067617 | 6/2008 | | |
| WO | WO-2024042468 A1 * | 2/2024 | ........... | A61B 8/4416 |

OTHER PUBLICATIONS

Extended European Search Report and Search Opinion received for EP Application No. 25161734.6, mailed on Jul. 16, 2025, 8 pages.

* cited by examiner

200 - A method to produce segregated images of anatomical structure(s)

- 210 → determine a volumetric field of regard (FOR) of the imaging device relative to the patient
- 220 → provide a model of at least a portion of a body anatomy present in the FOR
- 230 → determine a region of interest in the FOR occupied by the portion of a body anatomy
- 240 → adjust capturing parameters of the imaging device for capturing segregated image of the ROI
- 250 → Obtain and render the volumetric image of the ROI

*FIG. 3B*

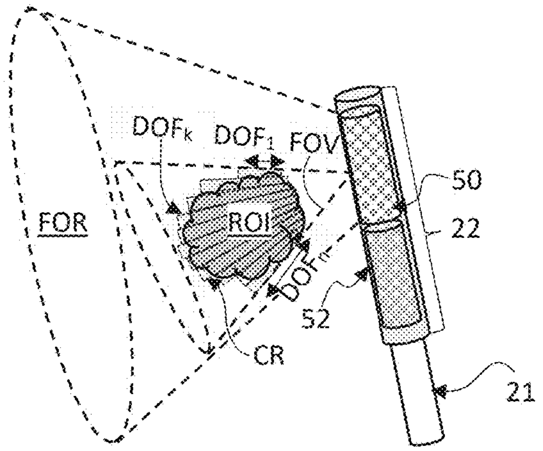

*FIG. 3C*

400 - A method to produce segregated images of anatomical structure(s)

ULTRASOUND SYSTEMS AND METHODS FOR LOCATION-BASED MEDICAL ILLUMINATION OF A REGION OF INTEREST WITHIN A DIMINISHED FIELD OF VIEW

TECHNOLOGICAL FIELD

The present invention generally relates to imaging and medical visualizing methods, and particularly to visualization of anatomical structure acquired by an intra-body medical imaging device such as an ultrasound probe.

BACKGROUND

Three-dimensional (3-D) images as well as four-dimensional (4-D) images (i.e. 3D video sequence) of anatomical structures, such as ultrasound images/videos of a heart, are useful in many catheter-based diagnostic and therapeutic applications. Real-time imaging improves physician performance and enables even relatively inexperienced physicians to perform complex surgical procedures more easily. Three-dimensional imaging also reduces the time needed to perform some surgical procedures.

Some systems use hybrid catheters that incorporate position sensing. For example, U.S. Pat. No. 6,690,963 to Ben-Haim et al., which is assigned to the assignee of the present invention, and whose disclosure is incorporated herein by reference, describes a locating system for determining the location and orientation of an invasive medical instrument.

A catheter with acoustic transducers may be used for non-contact imaging of the endocardium. For example, U.S. Pat. No. 6,716,166 to Govari, and U.S. Pat. No. 6,773,402 to Govari et al., which are assigned to the assignee of the present invention, and whose disclosures are also incorporated herein by reference, describe a system for 3-D mapping and geometrical reconstruction of body cavities, particularly of the heart. The system uses a cardiac catheter comprising a plurality of acoustic transducers. The transducers emit ultrasound waves that are reflected from the surface of the cavity and are received again by the transducers. The distance from each of the transducers to a point or area on the surface opposite the transducer is determined, and the distance measurements are combined to reconstruct the 3-D shape of the surface. The catheter also comprises position sensors, which are used to determine location and orientation coordinates of the catheter within the heart.

Typically, such systems provide an "endoscopic view", in which a reconstructed image is presented as it would appear if viewed through a certain catheter or other probe. For example, U.S. Pat. No. 6,556,695, to Packer et al., whose disclosure is incorporated herein by reference, describes a method for producing high resolution real-time images of a heart. During a medical procedure such as endocardial physiology mapping and ablation, real-time images are produced by an ultrasonic transducer inserted into the heart. A high-resolution heart model is registered with the acquired real-time images and is used to produce dynamic, high-resolution images for display during the procedure. Different parts of the anatomy may be viewed by moving a catheter distal end to "aim" an acoustic transducer at structures of interest. A joystick may be used to scan away from the field of view of the ultrasonic transducer when other parts of the anatomy are to be examined without moving the catheter. An orientation within the anatomic structure (e.g. heart chamber) is maintained using navigation icons as described in U.S. Pat. No. 6,049,622, to Robb et al., whose disclosure is also incorporated herein by reference.

Similarly, U.S. Pat. No. 6,203,497, to Dekel et al., whose disclosure is also incorporated herein by reference, describes a system and method for visualizing internal images of an anatomical body. Internal images of the body are acquired by an ultrasonic imaging transducer, which is tracked in a frame of reference by a spatial determinator. The position of the images in the frame of reference is determined by calibrating the ultrasonic imaging transducer to produce a vector position of the images with respect to a fixed point on the transducer. This vector position can then be added to the location and orientation of the fixed point of the transducer in the frame of reference determined by the spatial determinator. The location and orientation of a medical instrument used on the patient are also tracked in the frame of reference by spatial determinators. This information is used to generate processed images from a view spatially related to the location of the instrument.

U.S. Pat. No. 7,020,512, to Ritter et al., whose disclosure is incorporated herein by reference, describes a method of localizing a medical device inside a patient's body. AC magnetic signals of different frequencies are transmitted between points of known location outside of the patient's body and points on the medical device inside the patient's body. The transmitted AC magnetic signals are then processed to determine the position of the points on the medical device, and thus the location of the medical device. This processing includes correcting for the effects of metal in the vicinity by using the transmitted and received signals at different frequencies.

U.S. Pat. No. 7,020,512 also describes an alternative embodiment, in which a reference device is provided inside the patients' body, and the medical device is localized relative to the reference catheter. The use of signals comprising at least two frequencies may or may not be used in this relative localization embodiment, but typically are used at least to localize the reference catheter.

U.S. Pat. No. 10,299,753 to Govari et al., which is assigned to the assignee of the present invention, and whose disclosure is incorporated herein by reference, discloses a method for imaging an anatomical structure on a display, including acquiring an initial spatial representation of the anatomical structure and positioning an instrument in proximity to the anatomical structure. The method further includes determining a location of the instrument, and generating, in response to the location, an image of a part of the anatomical structure. The method includes appending the image to the initial spatial representation to display a combined spatial representation.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A to 2C depict medical images processed by the technique of the present invention in which: FIG. 2A presents an initial/preprocessed image of an anatomical structure, FIG. 2B is a segregated image of the anatomical structure captured according to the technique of the present invention, and FIG. 2C presents a cropped image of the anatomical structure produced by the technique of the present invention;

FIGS. 3A and 3B are respectively a block diagram and a flowchart presenting a system and a method for acquiring segregated medical images of a body anatomy of interest according to embodiments of the present invention;

FIG. 3C schematically illustrates a fitting of a capturing region of a catheter's imaging device to a region of interest at which a body anatomy resides according to an embodiment of the present invention.

Like reference numerals are used in the figures below with reference to elements/operations in the figures which have similar configurations and/or functions.

DETAILED DESCRIPTION OF EMBODIMENTS

Images of anatomical structures, such as a heart, and in particular high dimensional images such as three or four dimensional (3-D or 4-D, collectively also written herein as n-D images) typically contain a huge amount of visual information, thus often making it difficult for a viewer to distinguish features of interest in the image from the surrounding background. The present invention addresses this problem and facilitates viewing of an n-D image that presents a specific anatomical structure of interest or a portion thereof, substantially separated/cleared from surrounding body tissues, fluids or other anatomical structures. To this end, embodiments of the present invention provide systems and methods for capturing segregated images of anatomical structure(s) of interest substantially cleared from its surrounding background, and/or for processing captured images in which the anatomical structure of interest is present to produce therefrom cropped images of the anatomical structure cleared from its surroundings. Some embodiments of the invention facilitate a viewer, typically a system operator or a physician, to select an anatomical structure of interest or part thereof whose image is to be produced, and utilize a corresponding model of the anatomical structure to capture segregated image thereof, and/or to crop the images thereof, such that the segregated or cropped images presenting the anatomical structure (also referred to herein body anatomy), or portion(s) thereof without, or with diminished surroundings.

Embodiments of the present invention may be used for viewing images of different anatomical structures or portions thereof as wells as anatomical structures comprising cavities. Hereinbelow, by way of example, the anatomical structure is assumed to comprise the heart of a patient or parts thereof.

Figure 1:
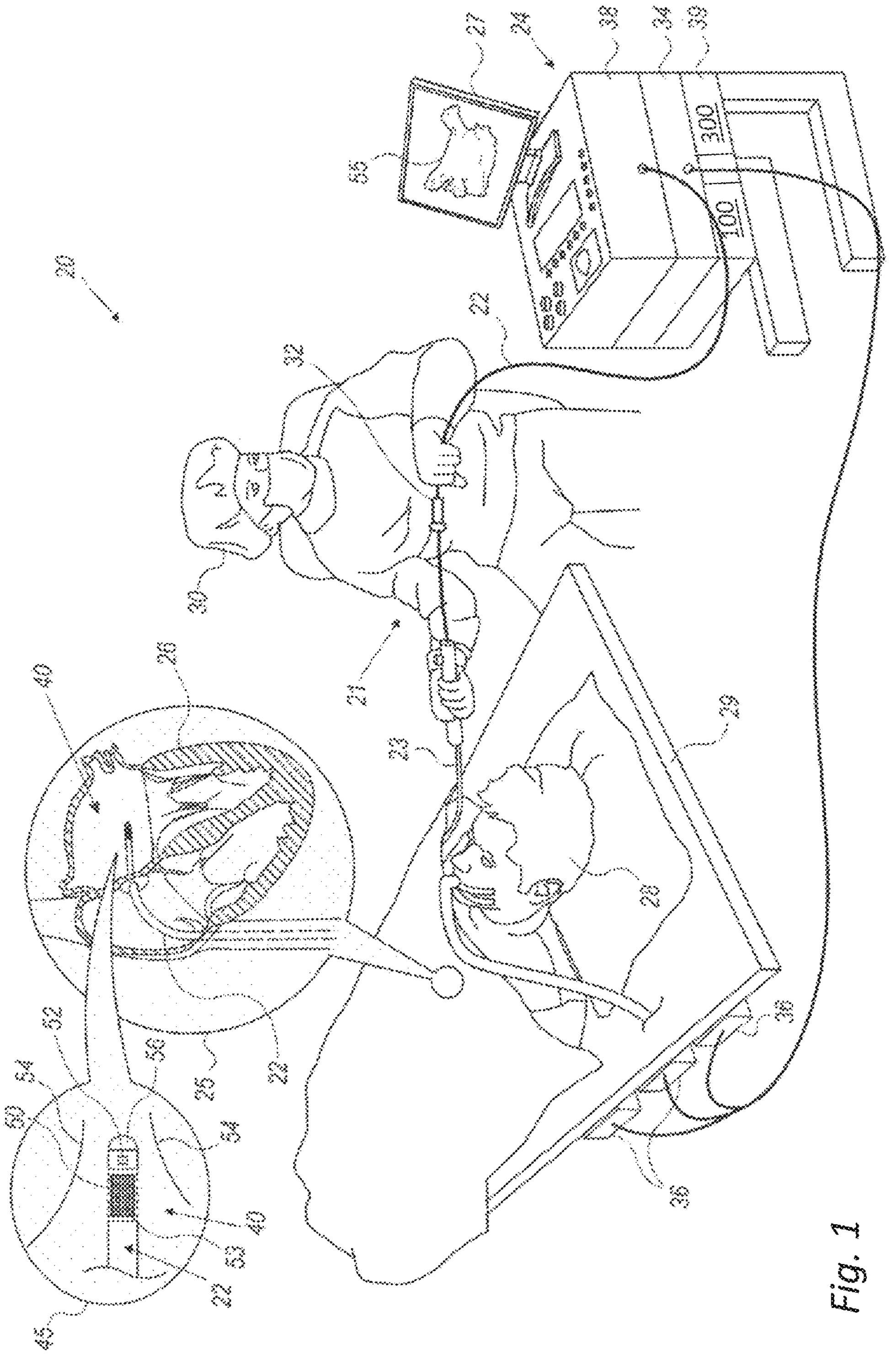
FIG. 1 is a schematic, pictorial illustration of a catheter-based ultrasound imaging system using a catheter having a distal end assembly that includes a 2D ultrasound-array and a location sensor, in accordance with an embodiment of the present invention.

FIG. 1 is a schematic, pictorial illustration of a catheter-based imaging system 20. In accordance with an embodiment of the present invention, the system 20 utilizes a catheter 21 having a distal end assembly 40 including an imaging device 50 and a position sensor 52 capable of providing data indicative of the location and orientation the imaging device 50 imaging device.

Specifically, position sensor 52 is configured to output signals indicative of a location and orientation of the imaging device 50 within a patient's 28 body (e.g., inside an organ thereof). The imaging device 50 may be configured and operable to implement any one of various medical imaging technologies, for example ultrasound imaging.

In the specific none-limiting example shown in FIG. 1, the distal end assembly 40 of the catheter 21 is located at the distal end of a shaft 22 of the catheter 21. The Catheter 21 is shown to be inserted through a sheath 23 into a heart 26 of a patient 28 lying on a surgical table 29. The proximal end of catheter 21 is connected to a control console 24. In the specific embodiment described herein, catheter 21 is used for ultrasound-based diagnostic purposes, although generally the catheter may implement other medical imaging technologies in addition to, or instead of ultrasound imaging, or it may be further be adapted to perform additional therapy operations, such as electrical sensing and/or ablation of tissue in heart 26, using, for example, one or more distal tip electrode(s) 56. Physician 30 navigates distal end assembly 40 of catheter 21 to a target location within the patient's body (in this example the patient's heart 26), for instance by manually manipulating shaft 22 using a manipulator 32 near the proximal end of the catheter 21, or by utilizing other catheter navigation technologies as known or will further be known in the art. Exemplary catheters and imaging assemblies that enable deflection and rotation are described in detail in U.S. Pat. Nos. 9,980,786; 10,537,306; and U.S. Patent Publication No. 2020-006134, whose disclosures are all incorporated herein by reference.

In an example embodiment shown in detail in insets 25 and 45, the imaging device 50 is arranged to image a left atrium of heart 26. As shown in the inset 45 the imaging device 50 in this example is an ultrasound imaging device including a 2D array of multiple ultrasound transducers 53 (e.g., 32×64 US transducers). Inset 45 shows the imaging device 50 navigated to an ostium 54 of a pulmonary vein of the left atrium. The imaging device 50 is able to image a section of the inner wall of the ostium. With the use of position data provided by the position sensor 52 and its registration with the imaging device 50, the system 20 can determine the spatial coordinates of every pixel/voxel in an imaged section obtained by the imaging device 50. An example of a suitable 2D ultrasound array is described in D. Wildes et al., "4-D ICE: A 2-D Array Transducer With Integrated ASIC in a 10-Fr Catheter for Real-Time 3-D Intracardiac Echocardiography," in IEEE Transactions on Ultrasonics, Ferroelectrics, and Frequency Control, vol. 63, no. 12, pp. 2159-2173 December 2016, doi: 10.1109/TUFFC.2016.2615602, which is incorporated herein by reference in its entirety.

It should be noted that the imaging device 50 is typically associated with, or includes, an imaging controller (e.g. such as 50A specifically exemplified in FIG.), that is adapted to control/adjust image capturing parameters of the imaging device, such as: its field of view (FOV), depth of field (DOF), imaging device, dynamic range, gain and/or sensitivity. Optionally incase an imaging device 50 has an active illumination, the imaging controller may also be adapted to adjust the intensity of the active illumination and/or gating time intervals of image capturing relative to the illumination timing. In various implementations the imaging device may be operated in snapshot mode in which the imaging device's entire FOV is captured instantaneously, and/or in scanning mode, in which the imaging device's FOV is scanned/steered to produce an image thereof. In such implementations, an imaging controller may be adapted also for controlling the snapshot and/or scanning modes' parameters. Further the imaging device 50 is typically also associated with, or includes, an image preprocessor (e.g. such as 50C specifically illustrated in FIG. 3A), that is adapted to process/combine image portions captured from the imaging device to produce therefrom n-D representation of an image captured by the imaging device. For example, the image preprocessor may be adapted to combine a plurality of 2D images of different FOVs taken at substantially similar times to produce thereby a volumetric (3D) image, and/or to combine a plurality of such volumetric images to form a video (4D image). Ultrasound catheters within the scope of the present invention may be 4D ultrasound catheter having a two-dimensional (2D) array of ultrasound transducers for producing three-dimensional (3D) or four-dimensional (4D) ultrasound images. In the present context, the term "3D ultrasound image" refers to an ultrasound image that represents a certain volume in three dimensions. The term "4D ultrasound catheter" refers to a catheter incorporating a 2D array of ultrasound transducers. The term "4D ultrasound image" refers to a time-series of 3D ultrasound images of a certain volume acquired by the 2D array. A 4D image can be regarded as a 3D movie, the fourth dimension being time. Another way of describing 4D image (or rendering) is as a time-dependent 3D image (or rendering). Where used in the heart, a 4D ultrasound catheter may be referred to as "4D Intracardiac Echocardiography (ICE)" catheter. The catheter may also comprise an integral location sensor, such as a magnetic position sensor, that is pre-registered with the 2D array based on the known relative position and orientation on the catheter shaft between the location sensor and the 2D array. The 2D array produces a 3D sector-shaped ultrasound beam occupying a defined solid angle; (such a beam is referred to herein as a "wedge," as opposed to a 1D array "fan"). The 2D array is thus able to image a 2D section of an inner wall of an organ, such as of a cardiac chamber. Because of the integral location sensor, and its pre-registration with the 2D array, the spatial coordinates of every voxel in the imaged section are known.

It should be understood that in some implementations, the imaging controller and/or the image preprocessor are collocated with (e.g., as integral part of) the imaging device 50, or in some embodiments the imaging controller and/or the image preprocessor may reside remotely from the image sensor(s) (which is referenced 50B in FIG. 3A), and for example may be implemented as part of the system 20 (e.g., part of a computerized system 39 thereof) or in separate system/driver.

Control console 24 of system 20 includes a computerized system 39, with suitable front end and interface circuits 38 for receiving signals from catheter 21, as well as optionally for applying treatment via catheter 21 and optionally for controlling the other components of system 20.

The position sensor 52 is typically associated with a positioning system 34 of system 20 that is capable of processing the position signals obtained from the position sensor 52 and determining thereby the position of the catheter's distal end assembly relative to the patient's body (i.e., which is indicative of the position of the imaging device 50 relative thereto). In some embodiments the position sensor 52 operates to sense signals indicative of its location and orientation (herein collectively referred to as position) based on magnetic/electromagnetic fields that are generated by magnetic/electromagnetic field generators 36. In such embodiments the positioning system 34 includes the magnetic field generators 36 and a driver circuit (not specifically shown), that is configured to drive the magnetic field generators 36 that generate magnetic fields utilizable by the position sensor 52 for sensing its position. Typically, the magnetic field generators 36 are placed at known positions external to patient 28, e.g., below table 29 upon which the patient 28 is lying. Accordingly, the magnetic fields produced thereby are usable as a reference coordinate frame for tracking the position of the catheter 21 within the patient's 28 body. For example, during the navigation of catheter's distal end 40, the position sensor 52 senses the magnetic fields provided by the magnetic field generators 36 and in response provides the system with position data/signals indicative of the position (location and orientation) of the catheter's 21 distal end 40. The position data/signals may be for example the magnetic field signals sensed by the sensors, and/or data/signals further processed from the sensed signals. Console 24 receives the position data/signals from position sensor 52 and thereby determines the location and orientation of the imaging device 50 within the patient's 28 body. A method of position and direction sensing using external magnetic fields is implemented in various medical applications, for example, in the CARTO™ system, produced by Biosense Webster, and is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

It should be noted that the system 20 is not limited to the specific magnetic/electromagnetic-field based positioning system described above, and can be alternatively or additionally be implemented with other position techniques, for instance by impedance-based location tracking, or by other techniques. Details of the impedance-based location tracking technology are described for instance in U.S. Pat. Nos. 7,536,218; 7,756,576; 7,848,787; 7,869,865; and 8,456,182.

As indicated above according to some embodiments of the present invention the system 20 is adapted to produce segregated images and/or cropped images of anatomical structure(s) of interest, to enable presentation of the same to an operator or physician 30 using the system.

In this connection, it should be noted that the phrase anatomical structure is used herein to refer to one or more portions of one or more body anatomies in the patient's body. Moreover, it should be understood that the phrase segregated image and cropped image are both used herein to designate an image presenting an anatomical structure of interest that is captured from the patient's 28 body, while with diminished presentation of other tissues/features that are not associated-with/belong-to the anatomical structure of interest (e.g. with diminished presentation of surrounding tissues/fluids and the like) so as not to obscure the presentation of the anatomical structure of interest. Specifically, the phrase segregated image is used herein to designate an image that is captured by the imaging device 50 with capturing parameters of the imaging device being adjusted so as to diminish capturing of the tissues/features/fluids that are not associated-with the anatomical structure of interest. The phrase cropped image is used to a captured image (segregated or not) which was further processed/cropped to remove/blank such features/tissues appearing therein that are not associated-with the anatomical structure of interest.

To achieve that the system 20 (e.g., the console 24) includes a system 100 and/or 300 according to the embodiments of the present invention, which are adapted to produce segregate/cropped images of anatomical structures of interest.

Systems 100 and/or 300, according to embodiments described in more details below, may be implemented as a computerized system, and may include hardware and/or software configured and operable for producing the segregated/cropped images. In some embodiments, system 100 and/or 300 may be implemented with the computerized system 39 of system 20. The computerized system 39 may for instance include a general-purpose computer or other computerized systems, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

System 100 may for example be connectable to the positioning system 34 (or the catheter's positioning sensors 52) and to the imaging device 50 of catheter 21 and adapted utilize position data/signals obtained from the position sensor/system 52/34 to operate the imaging device 50 for capturing segregated image(s) of anatomical structure of interest. System 300 may for example be adapted to the obtain an image (e.g. captured by the imaging device 50), together with position data indicative of the position within the patient's body from which the images were captured as well as optionally capturing parameters of the imaging device 50 by which the image was captured, and processed the image based on the position data (optionally also using the capturing parameters) to yield a cropped image of the anatomical structure of interest.

In this regard, in some embodiments of the present invention the system 100 and/or 300 facilitate automatic generation of respectively segregated or cropped images of an anatomical structure captured by the imaging device 50, based on the position of the imaging device when the image is taken. Indeed, once an image that is captured from a certain position within the patient's body is obtained by the system 100 or 300, together with position data indicative of that position, the system 100 or 300 may operate to automatically determine which anatomical structure(s) should be present in the image. This may be based on the position data of the image, which may be used to assess the field or regard (FOR) within the patient's body from which the image was taken, and optionally also based on data indicative of the imaging device's capturing parameters associated with the image, which may be used to more accurately assess the actual captured region (CR), within the patient's body, which is being captured in the image. Accordingly, system 100 and/or 300 may be facilitated with data access to a knowledgebase indicative of the locations/positions/models of various anatomical structures within patients' bodies, and may be adapted to utilize the FOR/CR data inferred based on the imaging device's position and optionally its capturing parameters, to infer from the knowledge base which anatomical structure(s) should be present in the image.

Figure 2A:
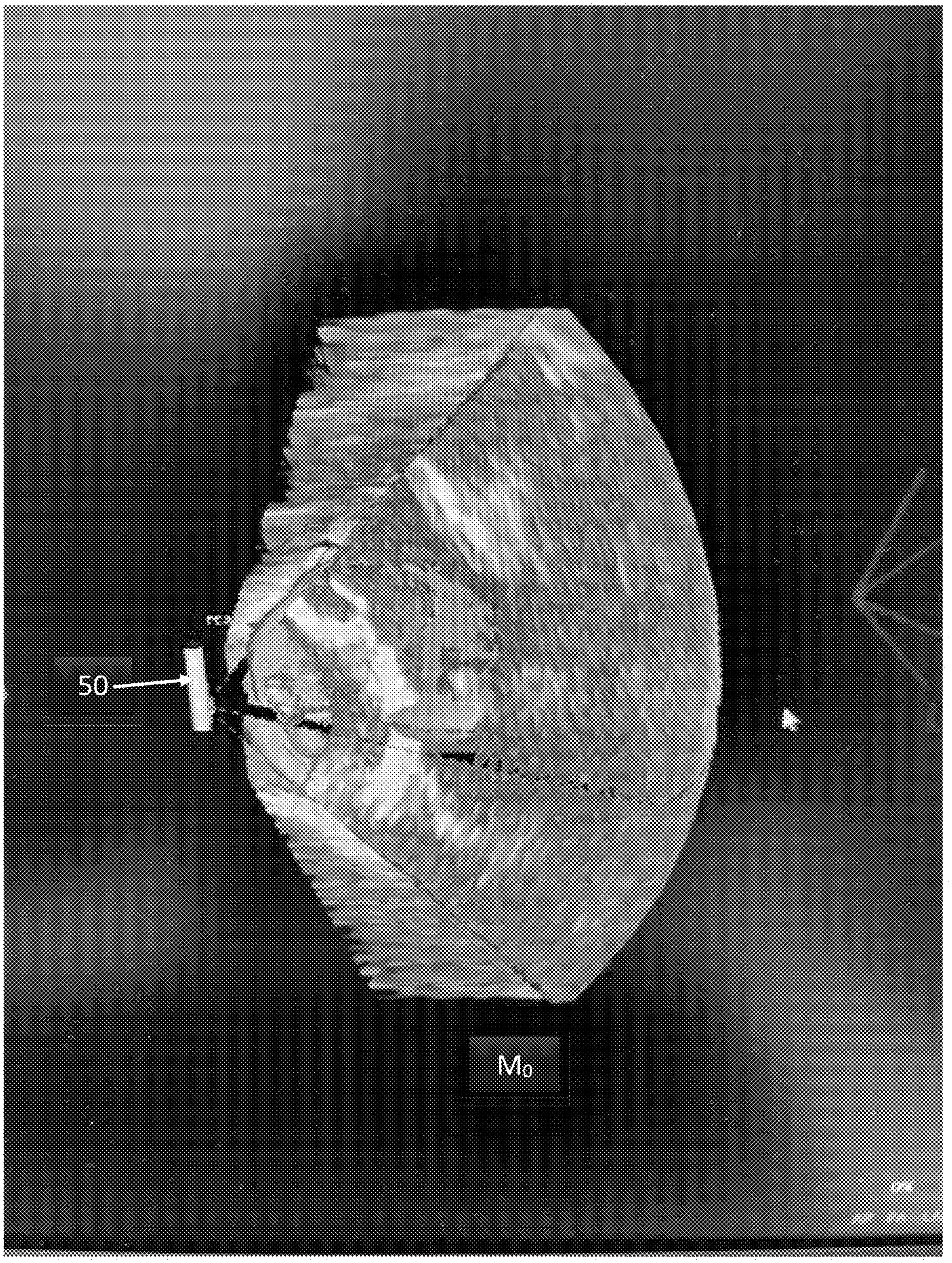
Figure 2B:
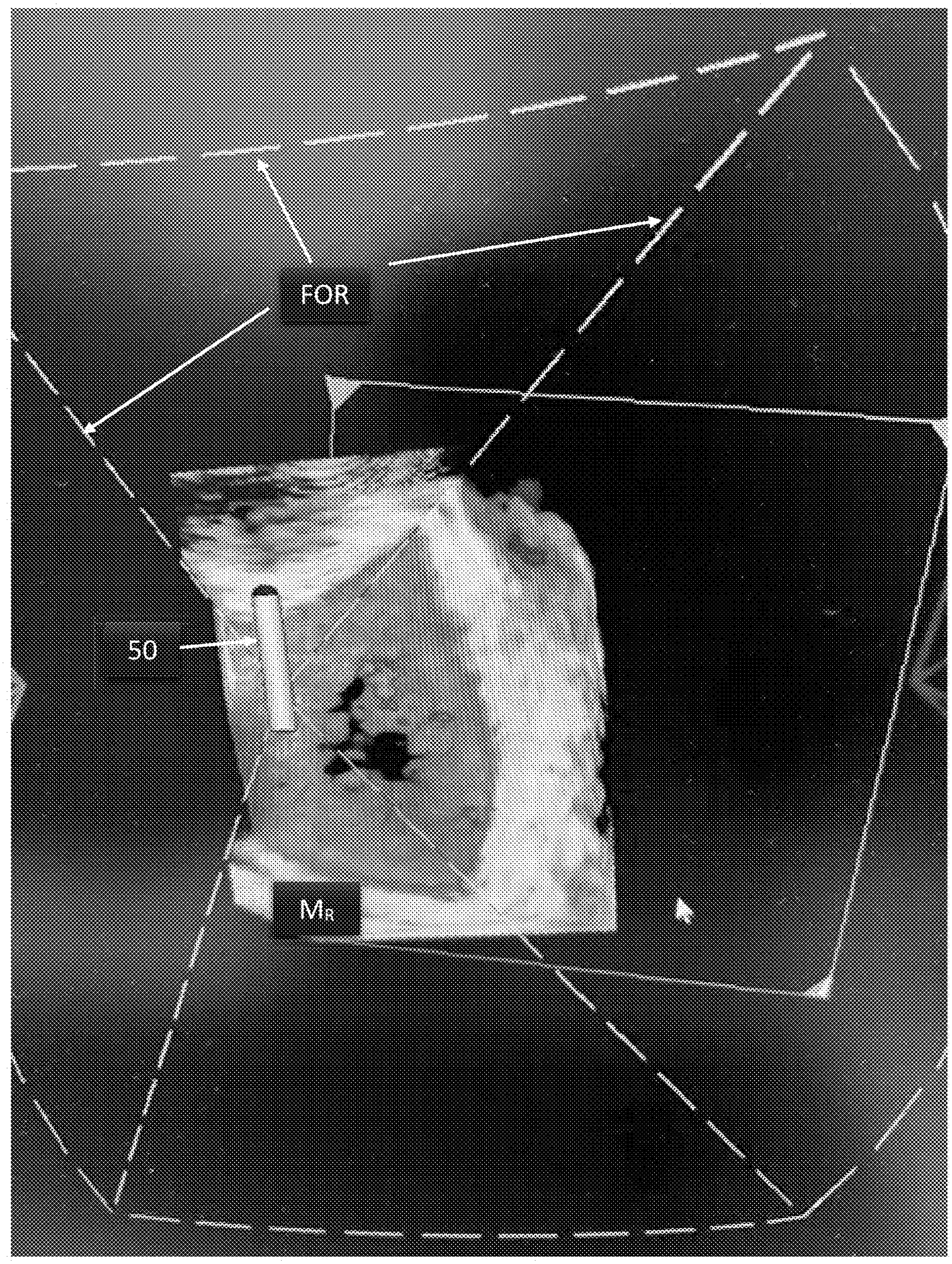

With reference to FIGS. 2A, an example of an image $M_0$ (also referred to in the following as an initial image), which is captured from the FOR of the imaging device 50 when positioned at a certain position within the patient's body, is illustrated. In this non limiting example, the initial image $M_0$ is a volumetric/3D image of the entire imaging device's FOR taken from within a patient's heart during preparation to a transeptal procedure. In this initial image $M_0$, the Fossa Ovalis is captured but is obscured by other tissues in its surrounding (e.g. tissues of the tissues in the near-field and or far-field from the Fossa Ovalis relative to the imaging device). FIG. 2B exemplifies a segregated image $M_R$ of the Fossa Ovalis as obtained by the operation of system 100. In this example the Fossa Ovalis was automatically targeted as the anatomical structure of interest by the system 100, based on the position data of the imaging device 50. To this end, it should be noted that based on the position of the imaging device 50, and optionally also based on the capturing parameters thereof, any of the systems 100/300 may automatically 'know' (e.g. utilizing the knowledge base) the location of the imaging device's 50 FOR within the patient's body (e.g. in this example 'know' that imaging device 50 'looks' from the right atrium into the left atrium—from R to L) and optionally also determine the anatomical structure to which the imaging device is focused/tuned-to-capture (e.g., utilizing the capturing parameters of the imaging device).

Figure 2C:
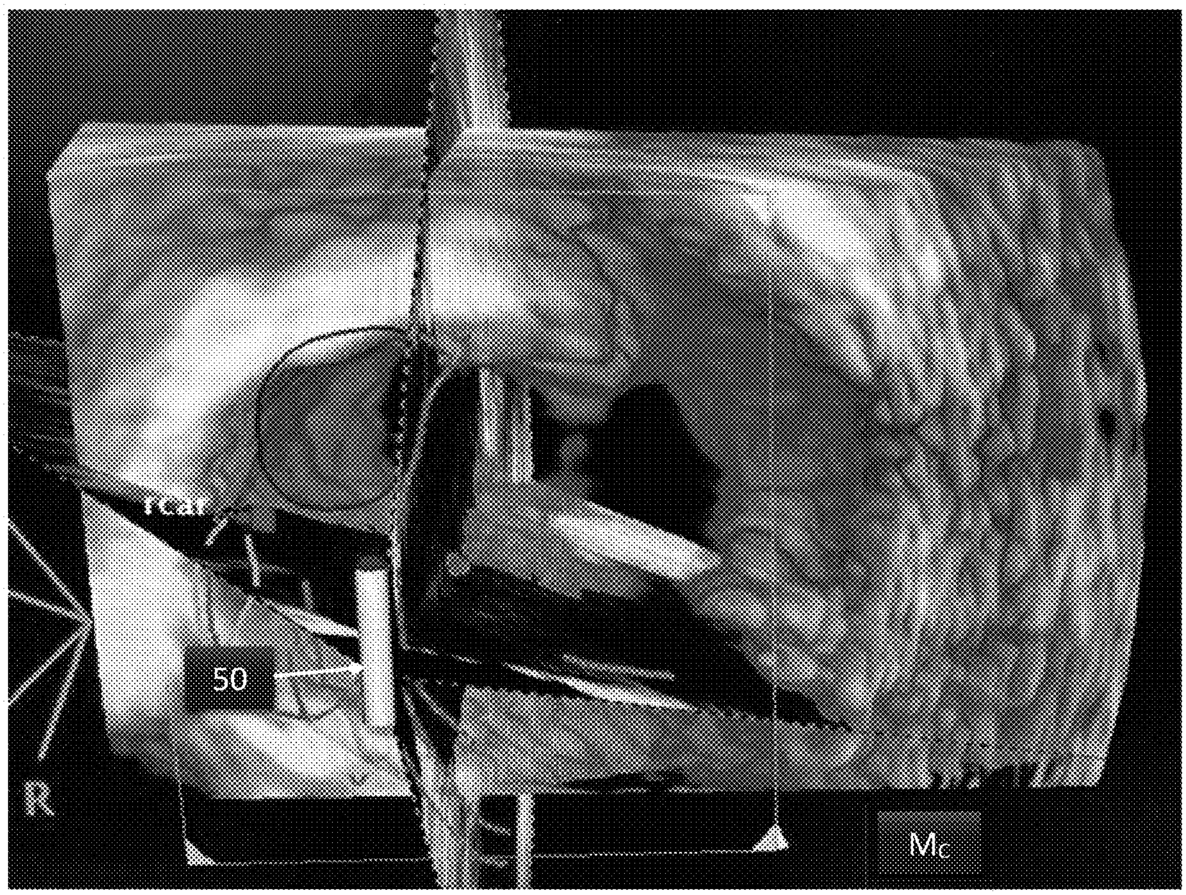

Accordingly system 100 may optionally automatically determine/assess the anatomical structure of interest (target) based on the location of the imaging device and optionally other capturing parameters thereof, and thereby optionally operate to automatically produce cropped/segregated imaging devices thereof. In the example of FIGS. 2A to 2C the imaging device was focused/tuned to capture an anatomical structure of interest (target) that is relatively close to the imaging device 50—which is in this case the Fossa Ovalis. In a similar manner, system 300, may also automatically determine the anatomical structure of interest from the initial image $M_0$ and may be adapted/operated to automatically crop the initial image $M_0$ itself, or another image grabbed from the imaging device 50, to the structure of interest (for instance by removing from the initial image $M_0$ voxels that are on the sides of the anatomical structure of interest and/or removing close & far field voxels that are in-front and behind the structure of interest relative to the location of the imaging device when grabbing image $M_0$).

FIG. 2B, shows a segregated image $M_R$ obtained as a result of the system 100 being adapted/operated to (e.g. automatically) capture a segregated image of the Fossa Ovalis, which was set (e.g. manually), or otherwise automatically determined by the system, as the anatomical structure of interest in this case (e.g., such automatic determination may be based on the position data and optionally also on the capturing parameters of the imaging device 50 when capturing the initial image $M_0$ shown in FIG. 2A). To this end, in order to obtain the segregated image $M_R$ the system 100 operated to adjust capturing parameters of the imaging device 50 such as its Field-of-view, Depth-of-Field, and sensor's gain to optimize capturing of the anatomical structure of interest (Fossa Ovalis) from the position the imaging device is located at, while with diminished capture of its surroundings. The dashed white lines in the image are provided herein to illustrated the imaging device's FOR, which was captured in its entirety in the initial image $M_0$ shown in FIG. 2A. In the segregated image $M_R$ the Fossa Ovalis, being the structure of interest, is captured by system 100 by adjusting the imaging device's 50 capturing parameters.

In some embodiments of the present invention the system 100 and/or 300 facilitates user selection of the specific anatomical structure of interest of which a respectively segregated or cropped image will be generated. To this end, optionally, the system 100 and/or 300 is associated-with/connected-to user interface devices (e.g., display 27 and user input controls of console 24) and is adapted to receive thereby, from the operator, data indicative of the anatomical structure whose image is to be segregated/cropped. For instance, in embodiments, an initially a non-segregated/non-cropped image such as $M_0$ shown in FIG. 2A, that is captured by the imaging device 50 from a position at which the catheter 21 is located, may be presented to the physician on the display 27. The initial image $M_0$ may be for instance a 3D/volumetric image as shown in FIG. 2A (e.g. in which the physician/operator may navigate or slice to identify the structure of interest to him), or a 2D image, such as a 2D slice of an image captured by the imaging device 50 (e.g. an ultrasound image slice). The operator may then mark/select one or more points or regions on the initial non-segregated image indicative of at least one anatomical structure, that segregated image(s) thereof he would like to be produced. In various implementations the selection may for example be made by marking(s) of one or more points/boundaries (e.g., rough boundaries) on the presented image designating the anatomical structure of interest; or by selection from a list of anatomical structures (e.g., a list of anatomical structures that are automatically determined as expected to be included in the image (e.g., or in the FOR of the imaging device), for instance based on the knowledge base and the imaging device's position. Based on the selection(s)/marking(s), and the position at which the catheter 21/imaging device 50 resides relative to the patient's body (typically within it), the system 100/300 determines the anatomical structure(s) of interest, which is to be imaged in segregated from, or be cropped from the initial image $M_0$.

In this connection FIG. 2C, exemplifies an image $M_c$ cropped from the initial image $M_0$ that is illustrated in FIG. 2A, based on a user's selection. Indeed, in this case automatic identification of the anatomical structure(s) of interest based on the imaging device's position and capturing properties of the initial image $M_0$ might have identified the Fossa Ovalis as the anatomical structure(s) of interest (as indicated with reference to FIG. 2B). However, in this case the user/operator was actually specifically interested in viewing more clearly (in segregated/cropped form) the left pulmonary veins which also appear in the initial image $M_0$. Accordingly, the operator in this case utilized the user interface to mark/select the specific anatomical structure of interest (left pulmonary veins) he wishes to view, and the system 300 cropped the initial image $M_0$ (or for that matter another image might also have been used) according to this selection. It should be noted that such cropping may also be carried out on another image, and/or may be carried for example by system 100, optionally on an already segregated image acquired/produced thereby. Alternatively, or additionally, it should be understood that in a similar manner system 100 may also be adapted to obtain user selection (e.g. from a user interface) and produce segregated images of anatomical structures selected thereby.

As will be described in more details below, systems 100 and/or 300 utilize models, such as a morphological model or a machine learning model, for producing the segregated/cropped images of the anatomical structure of interest. Based on the automatically identified and/or user-selected, anatomical structure of interest, the systems 100 and/or 300 retrieve a suitable model therefore and utilize the same for the capturing of segregated image(s) and/or for cropping captured images.

System 100 according to an embodiment of the present invention will now be described in more detail with reference to FIGS. 3A and 3B, in which a block diagram and a flow chart are provided to exemplify the configuration of and operation of the system 100. System 100 adapted to produce segregated images of anatomical structure(s). System 100 is connectable to a catheter 21 having the imaging device 50 and the position sensor 52 furnished at the distal tip 40 thereof.

Imaging device 50 is capable of capturing volumetric images of a desired FOV and desired depth(s) of field (DOF) within its field of regard (FOR). For clarity and without limitation in the none limiting example of FIG. 3A, the imaging device 50 is shown to include three functional components including:

(i) the image sensor 50B, which may include one or more image detectors/transducers (e.g. sound/ultrasound transducers in case of ultrasound imaging device, and/or light or other type of electromagnetic field detectors in case of other types of imaging devices); as well as optionally an image scanning utility in case scanning scheme is employed by the imaging device; optionally an active illumination utility in case active illumination is employed by the imaging device; optionally imaging "optics" (suited for the field types sensed by the imaging device, be it sound or electromagnetic (e.g. light)) or other beam forming utilities for forming image signals by the signals of the detectors.

(ii) an imaging controller 50A, which is adapted to adjust one or more operational parameters of the imaging devices affecting the extent of the region CR that will be captured by the imaging device 50 when operated; and (iii) an image preprocessor 50C, that processes on the signals received from the image sensor 50B during image capture to construct therefrom a volumetric image of the captured region CR. As will be appreciated by those versed in the art of imaging the image preprocessor may be adapted to perform various image processing operation, which may depend on the specific configuration of the imaging device 50 and imaging scheme used, and said operations may include for example: stitching of image slices obtained during image scans to obtain the volumetric image result; our other operations such as equilibration of signals acquired from the different image detectors/pixels, determining of voxels depth position based on the time difference between pulses of active illumination (if used in the imaging device) and the sensed signals; determining the lateral position of voxels based on the concurrent scanning the sensed signals are associated with; and/or beamforming the sensed signals to construct the volumetric image or voxels thereof. To this end, the imaging device 50 used in this embodiment of the invention may be any type of imaging device permitting certain control of the location and extent/span of region CR within the imaging device's field for regard that will be captured by the imaging device.

In this example and without loss of generality, an ultrasound imaging device is specifically exemplified.

The position sensor 52 is capable of providing position data indicative of a position of the ultrasound imaging device 50 within the patient's 28 body. In the following the imaging device 50 in combination with the positioning system 34 is also referred to as tracked imaging system (101 in FIG. 3A and/or 301 in FIG. 4B), which is adapted for providing/capturing/storing the images processed by the system along with respective position data and optionally also data of the capturing parameters by which they are captured, which is indicative of the region CR within the body that is captured by the respective images.

Based on the position data, the system 100 is configured and operable to operate the imaging device 50 for capturing one or more 2D and/or 3D images of at least a portion of a body anatomy (anatomic structure) such that the 2D and/or 3D segregated images present the at least a portion of the body anatomy substantially segregated from other body tissues (e.g. nearby tissues), which are not associated therewith. To achieve that the system 100 is adapted to adjust one or more capturing parameters of the imaging device, such as its FOV and/or DOF or other imaging parameters, such that the region CR being captured by the imaging devices fits closely to the region of interest ROI within the patient's body which is occupied by the portion of a body anatomy whose capturing is desired.

In this connection it should be noted that the phrase field of regard (FOR) is used herein to designate a volumetric region in-front of the imaging device's 50 position, that the imaging device 50 is capable of capturing/perceiving when positioned thereat. It should also be noted that the terms field of view (FOV) and depth of field (DOF) are used herein to designate the capturing parameters and are indicative of the actual capturing region CR within the FOR that is captured by the imaging device's 50 sensor(s)/transducer(s). More specifically the term FOV pertains to the lateral/angular extent of the region captured by the imaging device 50 (e.g. lateral relative to the general direction/axis the imaging device 50 is directed to capture, which may be fixed or steerable relative to the imaging device's 50 sensor(s) e.g., depending on the imaging device's 50 configuration). The term DOF is used herein to designate the span between the nearest and furthest points in the captured region CR that appear to be acceptably focused/"sharp" in the captured image. In this regard for some types of imaging devices 50 usable by the system 100 (e.g., imaging devices operation via scanning of the region of interest) the DOF may be setup individually for each pixel, or group (e.g. row) of pixels in the image to be captured, as illustrated for instance in FIG. 3C. In some embodiments, particularly when the imaging device 50 incorporates active illumination and respective time gating capabilities for echo sensing, the system 100 may be adapted to exclude or diminish capturing of regions in-front or past the desired DOF, e.g. by proper time gating. Similarly, for some types of imaging devices 50, the cross-section of the FOV being captured by the imaging device, may be set up by system 100 to have a non-regular/non-a-priory-fixed shape. Accordingly, various embodiments the system 100 may be adapted to adjust the FOV capturing parameter and/or the DOF capturing parameter, to fit the capturing region CR to the anatomical structure of interest (e.g. in some cases the shape of the capturing region CR may be morphically fitted. This facilitate adjustment of such parameters such that the shape of the capturing region/volume CR substantially fits an anatomical structure of interest in the patient's body that is located there, while regions outside the designated capturing region/volume CR at which the anatomical structure of interest is located are excluded from the capture, or captured with diminished intensity in the image.

It should be noted that the terms illumination and active-illumination are used herein to designate any type of illumination used by the imaging device during capture, and may pertain for example to ultrasound illumination in the particular case of ultrasound imaging device 50, and/or to other types of active illumination (e.g. optical light or any other type of electromagnetic field/radiation as may be used by various types of imaging devices to illuminate the capture region). The terms, gating, gated, time-gating and the like are used herein to designate an operational mode of an imaging device in which the sensor or pixels (e.g. sub-sensors/detectors/transducers) thereof are operated in synchronization with the timings of the active illumination so as to sense echoes/reflections of the active illumination which arrive only from a certain DOF relative to the sensor (or relative to pixels thereof).

Moreover, it should be noted that with imaging devices of the type using beam steering and/or beamforming of either an active illumination or of the echoes/reflections received/sensed by the image sensors, the beam steering/forming scheme may be controlled adjusted by the system 100 to control the actual shape the region CR being captured. For instance, when beam forming is used on the active illumination, the active illumination may be beam-formed to illuminate/focus-on only certain parts within the FOR thus such that the capturing only includes those illuminated parts. Similarly, alternatively or additionally, when beam-forming is applied to the returning echoes/reflections, the focal points of the beam-formed echoes/reflections may be set to echoes arriving only from certain parts within the FOR (e.g. such that those echoes interfere constructively) while echoes/reflections from other FOR parts are diminished (e.g., via destructive interference), such that the capturing only includes those parts that are in the focuses of the echoes' beamforming. In like manner, beam steering, may also be used to control the cross-section shape of the FOV.

Additionally other capturing parameters of the imaging device, such as the sensor(s)'/transducer(s)' gain(s) and/or the operational dynamic range thereof, and/or the illumination intensity/frequency (in case active illumination is used) may be set/optimized to for producing/sensing echoes/reflections arriving from certain selected regions or body tissue-types with the FOR, while causing echoes/reflections from other regions/tissue-types to be produced/sensed with lower intensity.

Figure 3A:
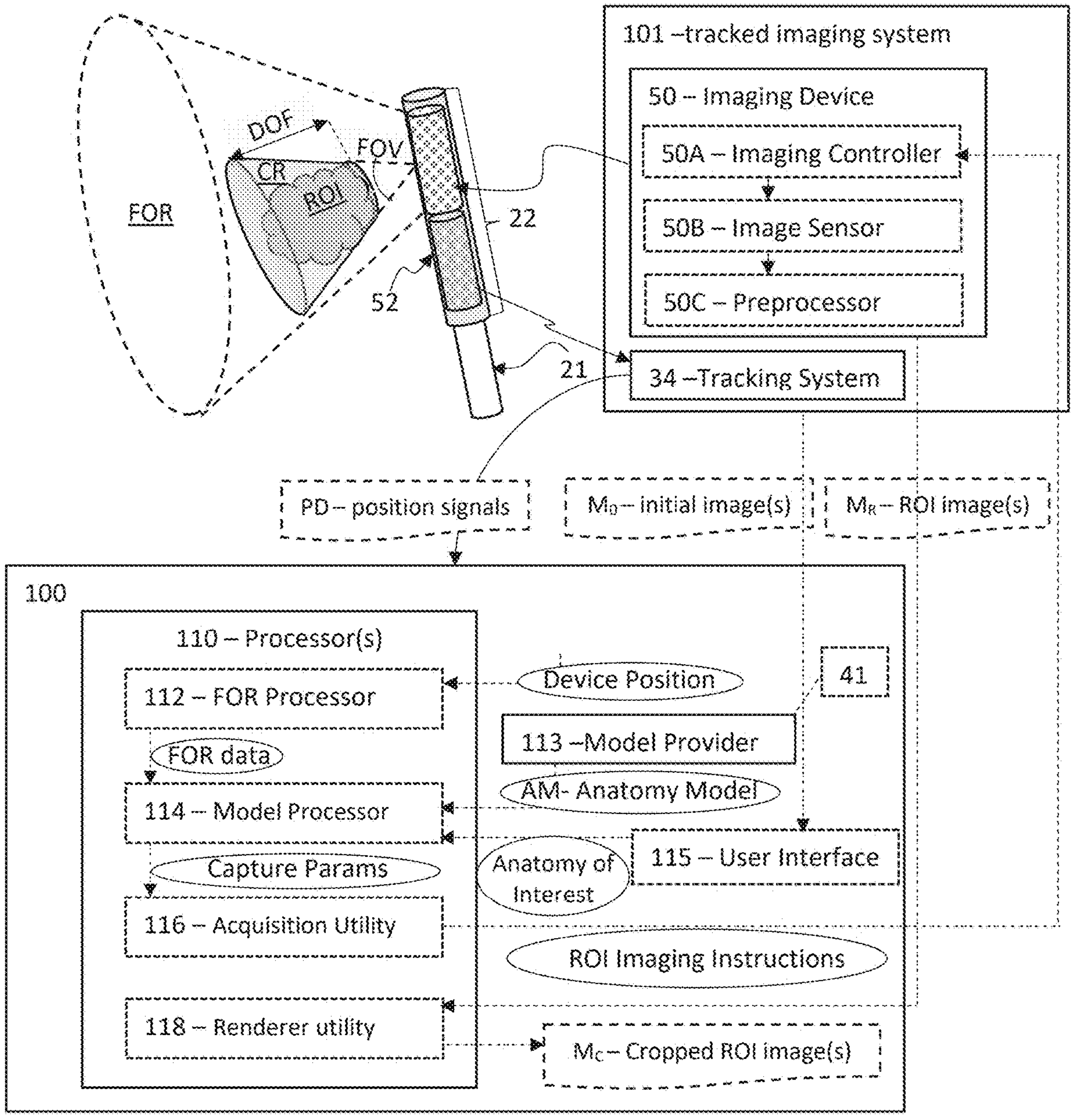

To this end, embodiments of the present invention, as described for instance with reference to FIGS. 3A to 3B, take advantage of the fact that capturing parameters which are adjustable in various imaging technologies, permit adjusting the size and/or shape and/or location, of the capturing region CR such that it fit relatively closely to a shape of an anatomical structure of interest, while maintaining most of the FOR regions outside the "fitted" capturing region CR excluded-from (diminished-in) the captured image. Accordingly, by identifying and anatomical structure of interest or portion thereof whose imaging is desired, and determining the region the anatomical structure of interest occupies within the imaging device's FOR, the imaging parameters (one or more of them) can be adjusted such that the captured region CR of the imaging device fits the anatomical structure of interest and thereby facilitate segregated capturing of the anatomical structure.

To achieve that, the system 100 includes one or more processing utilities 110 that are configured and operable to produce one or more 2D and/or 3D segregated images of at least a portion of a body anatomy of interest. The one or more processing utilities 110 of the system 100 may be implemented by software and/or by hardware, and may for example conceptually include the following functional processing utilities (which may be implemented in practice by one or more processors):

- A field of regard (FOR) processing utility 112 that is connected directly or indirectly (e.g. via the positioning system 34) to the position sensor 52 of the catheter 21, and adapted to process the position data received from the positioning system 34/position sensor 52 to determine a volumetric field of regard FOR extent of the imaging device relative to the reference coordinate frame of the positioning system 34. As the patient's body is generally registered with the positioning system 34 (e.g., by virtue of the location-pad/location-field generators 36 of the positioning system 34 being arranged at predetermined position relative to the patient's body), the volumetric field of regard FOR is actually determined relative to the patient's body.
- A model provider utility 113 is adapted to provide a model indicative of at least a portion of a body anatomy of interest whose capturing is desired. The model provider may be adapted to provide one or more models of anatomical structures that are expected to be present within the volumetric FOR of the imaging device 50 in the patient's body, and/or a model of a specifically selected anatomical structure (or portion thereof), which is selected by the physician/operator via the user interface 115, described below.

An optional user interface (UI) 115 (e.g. including a display and UI input controls) that is adapted to enable a user to select a region of interest within the imaging device's FOR at which resides an anatomical structure or portion thereof whose segregated imaging is desired.

A model processing utility 114 adapted to receive the model of the anatomical structure of interest from the model provider, as well as inputs from the imaging device indicative of image content captured from the FOR, and utilizing the model to image content to identify the region of interest ROI at which the anatomical structure of interest resides in the FOR.

Capturing controller 116 is adapted to obtain data indicative of the ROI (its location and extent within the FOR), and adjust one or more capturing parameters of the imaging device 50 in order to optimize capturing by the imaging device 50 of the at least portion of the body anatomy, for reducing the acquisition of visual information captured from the background/tissues surrounding the at least portion of the body anatomy of interest. The capturing controller 116 adjusts the capturing parameters such that the captured region CR is fitted more closely to the region of interest ROI at which the body anatomy of interest resides in the FOR. This is achieved based on the processing made by the model processor 114 to determine the position/location of the body anatomy of interest within the imaging device's FOR based on the model AM. The capturing controller 116 is connected to the imaging device 50 (e.g. to the imaging controller therefor 50A) to adjust the imaging parameters accordingly for capturing the ROI with utilizing said imaging parameters.

An acquisition utility 116 is adapted to operate in response to the capturing of the ROI by the imaging device 50 with the capturing parameters, in order to obtain, from the imaging device 50 (e.g., from an imaging preprocessor 50C thereof), a segregated volumetric image of the anatomical structure of interest in the ROI, as captured with the adjusted parameters.

An optional rendering utility 118 is adapted to obtain the at least one segregated volumetric image of the anatomical structure of interest the ROI to yield one or more 2D and/or 3D segregated images of said at least portion of the body anatomy of interest, in which at least portion of the body anatomy of interest appears such that it is substantially segregated from body tissues not associated therewith.

The operation of system 100 will now be described in more details with reference to FIG. 3B, which is a flow chart of a method 200 to produce segregated images of anatomical structure(s) of interest, according to an embodiment of the present invention.

In operation 210 the volumetric field of regard (FOR) of the imaging device 50 relative to (e.g., within) the patient's 28 body is determined (e.g., by the FOR processor 112 indicated above) based on the position data obtained from the position sensor 52 (e.g., from the positioning system 34 associated therewith). Indeed, the positioning system (which is in communication with the position sensor 52 on the catheter 21) receives from the position sensor 52 signals/data that are indicative of the location and orientation of the distal end 40 of the catheter 21 at which the imaging device 52 resides. The positioning system 34 operates in registration with the patient's body, and thereby determines the location and orientation of the imaging device 50 relative/within the patient's body. This location and orientation data of the imaging device 50 together with predetermined data indicative of the imaging device's viewing capabilities (e.g., it's maximal FOV angle and maximal DOF extent), are processed to determine the FOR of the imaging device 50 within the patient's body.

In operation 220 a model of at least a portion of a body anatomy existing in the FOR is retrieved/obtained, e.g., by the model provider 113 of system 100. In some embodiments the model may be automatically retrieved based on the data indicative of the FOR of the imaging device 50 that is obtained in 210 relative to the patient's body, optionally also based the capturing parameters the imaging device is/was set to (by which the anatomy of interest to the physician may be assessed) and based on knowledgebase data (e.g. indicative of locations of various anatomical structures within the body) from which information indicative of anatomical structure(s) that is/are contained in the FOR can be determined/assessed (e.g. in accordance with the registration between the FOR and the patient's body).

Alternatively, or additionally, in some embodiments, in order to identify the at least portion of the body anatomy of interest more precisely, operation 220 may include: grabbing at least one image of the FOR or part thereof from the imaging device (see $M_0$—initial image(s) in FIG. 3A) and presenting the same on to the physician/operator of the system 100 and/or method (200). The initial image(s) $M_0$ may be presented for example via a user interface 115, or display thereof, and responsive to said presentation, the system may obtain from the physician/operator input data (selections/markings) indicative of a selected region of interest ROI or of a specific anatomical structure within the imaging device's FOR, that the physician/operator wishes to get segregated image of. In some implementations, the initial image(s) $M_0$ may be for example a 2D slice of the at least a portion of the imaging device's FOR, or a volumetric image thereof which the physician/operator can manipulate to display view a desired portion thereof by the UI 115.

Thus, based on the anatomical structures identified in the FOR of the imaging device, and/or based on the user selection/marking of the anatomical structure(s) of interest therein, and based on the position of the imaging device/FOR (as determined from the position data of the position sensor), the anatomical structure(s) of interest is identified, and the model provider 113 retrieves a corresponding model AM for the anatomical structure(s) of interest (e.g. from a data repository of anatomical structure models).

To this end, in some embodiments the model AM includes, or is constituted by, a morphological model of the anatomical structure(s) of interest (e.g., a so-called cloud of points model or other type of morphological model), which is for example indicative of at least one of its shape, size and optionally also its typical position within the body. Generally, such morphological model AM may be a generic morphological model of the anatomical structure of interest, or in some cases it may be a patient-specific morphological model. To this end, in case of a generic model AM, it may include data indicative of at least one of a characteristic shape(s), characteristic size(s) and/or characteristic position (s) of said at least portion of the body-anatomy/anatomical-structure of interest within. Alternatively, or additionally, such morphological model AM may be patient specific model indicative of the shape and/or size and/or position of the at least portion of the body-anatomy/anatomical-structure of interest for the specific patient 28. Yet alternatively, or additionally, such morphological model AM may be a condition specific model indicative of the shape and/or size and/or position of the at least portion of the body-anatomy/anatomical-structure of interest when having a specific condition/pathology from which the patient 28 is suffering.

In the latter case, such model may be a priory obtained/prepared (e.g., by the system) for example from prior imagery of the patient (such as from CT images or other types of medical images of the patient), or it may be pre-prepared (e.g. by the physician 30) by carrying out a mapping procedure that maps the anatomical structure of interest in the patient's body. In such mapping procedure, a physician may utilize for instance a "mapping" catheter (e.g. which may be the catheter 21 or a different catheter furnished with a position sensor such as 52) to map a plurality of locations on the anatomical structure of interest within the patient's body (whereby during said mapping the locations of the distal end of the catheter, and possibly other sensed properties such as tissue or ECG properties) are recorded in the model at points where the distal end of the "mapping" catheter is on the anatomical structure of interest.

To this end, in some embodiments the system 100 includes at least one mapping medical device 41 (e.g., mapping catheter) configured and operable for mapping anatomical structures in the patient's body. The mapping medical device 41 includes a position sensor thereon (not specifically shown) and is adapted to receive user input for mapping at least portion of a body anatomy. For instance, upon receiving user input indicative of that a location at which the catheter resides belongs to a body anatomy of interest (to be mapped), signals indicative of the same are provided to the system 100. The system 100 (e.g. one or more processors thereof, such as the model provider 113, and/or the positioning system 34) are adapted to track locations of the mapping medical device, and record the tracked locations thereof that are indicated as belonging to the body anatomy being mapped and thereby construct a patient specific model of the at least portion of the body anatomy of interest. In some implementations the system 100, e.g. the model provider 113 thereof, is adapted to record these tracked locations associated with the at least portion of the body anatomy of interest to form a model indicative of a shape of that portion of the patient's body anatomy (e.g. in the form of a cloud of points). Furthermore, optionally, in some implementations the mapping medical device 41 may include one or more sensors that are adapted to sense one or more tissues properties of the at least portion of the patient's body anatomy at these tracked locations, and the system 100 may include data indicative of the same in the model. More specifically tissue property data may include information indicative of the appearance of one or more tissues of various parts of the body anatomy and/or of its surrounding regions, when imaged by the imaging device 50.

Thus, in some embodiments the morphological model AM may also further includes tissue data indicative of certain property(ies) of one or more tissue types of the anatomical structure of interest. For instance, such tissue data may include spectral information indicative of tissue spectral response (absorbance/reflection/scattering) of different spectral regimes of the fields/radiation being imaged by the imaging device 50. The tissue data may include generic data indicative of tissue properties of generic anatomical structures of the type being recorder in the model, and/or of anatomical structures of this type which have a certain condition/pathology from which the patient is suffering, and/or patient specific tissue data obtained for example by the user of the mapping medical device/catheter 41 as described above.

Alternatively, or additionally, in various embodiments the model AM, which is retrieved by the model provider 113, may include a machine learning (ML) model that was trained for processing input data imagery (e.g. initial image (s) $M_0$ captured from the FOR), to output data indicative of the ROI region (e.g. its size shape and/or location) within the FOR at which the anatomical structure of interest resides (e.g. the region occupied by the anatomical structure of interest). The machine learning (ML) model may be used in addition to, or instead of, the morphological model described above. As will be appreciated by those versed in the art of machine learning, an ML model of this sort may include parameters (e.g. weights) of one or more neural network which were priorly trained to recognize and/or classify anatomical structure of the type of the anatomical structure being of interest within images (e.g. the initial image(s) $M_0$ grabbed from the FOR and determine the ROI therein occupied by the structure of interest. As will be also appreciated by those versed in the art after knowing the invention, a training of an ML model may be a priory conducted for each anatomical structure of interest for example by utilizing training data including a plurality of images in which the anatomical structure of interest appears, and adjusting the weights of the ML model (e.g., via gradient decent), until the model is trained to properly classify/recognize the ROI in the images in which the anatomical structure of interest resides. The training may be supervised, or partially-/un-supervised (whereby in the latter case morphological models, generic ones, or patient specific ones corresponding to the input imagery, may be used to correct and train the model in an unsupervised or partially supervised manner.

Thus, in operation 220 system 100 retrieves a model AM based on which the region of interest ROI at which the anatomical structure of interest resides/occupies can be identified in images obtained from the imaging device 50.

In operation 230 (e.g., which may be for instance performed by the model processor 114) the anatomical model AM is used to determine/assess the region of interest ROI within the FOR occupied by the anatomical structure of interest. The region of interest may for example be determined in terms of its size, shape, location and/or the "voxels" it occupies within the FOR. The model AM may be for instance a morphological model or a machine learning (ML) model as described above, and may be in some implementation a generic model of the anatomical structure or a personalized one.

In some implementations (e.g., for instance when the model is a morphological model) the system 100, or model processor 114 thereof, determines/assess the region of interest ROI by registering and/or fitting (e.g. so called "best fit") the model with one or more initial images grabbed from the FOR (e.g. the initial image $M_0$). In some embodiments, for example when the model is a generic model, or when the shape of the anatomy of interest varies (e.g. due to its motion), achieving the best fit between the model may for instance involve morphing/warping the model's shape to yield a morphed shape thereof, such that the morphed which is fitted to the grabbed initial images (e.g. such that most of the pixels/voxels presenting the anatomical structure of interest in the grabbed image(s), are "covered" by the morphed model, without covering pixels/voxels which do not present the anatomical structure of interest, or covering as few as possible of such pixels/voxels by the model). In this regard, as will be appreciated by those versed in the art after knowing the invention, the morphing/warping of the morphological model may be applied until a best fit is achieved or until certain morphing threshold are reached. The morphing/best-fit may be done based on partial image (s) of the FOR which may include only one or more 2D slices thereof or parts of volumetric image thereof. In embodiments where the morphological model includes data indicative of tissue properties of the anatomical structure of interest, these properties, which may include for instance the spectral response/properties of the tissues, may be used in the fitting/registration to determine the best fit (as far as they are apparent in the initial images $M_0$ based on which the model is fitted).

To this end, according to some embodiments, based on such fitting, the system 100, or model processor 114 thereof maps between the one or more regions (voxels) of the at least one body anatomy present in model AM and corresponding voxels (volumetric regions) within the FOR of the imaging device 50, thereby identifying the ROI occupied by the anatomical structure of interest within the FOR. Such mapping may be for example conducted based on a combination of one or more of the following:

- fitting of positions of between different regions (voxels) of the body anatomy in the model and corresponding pixels/voxels of within the FOR portion that is presented in the initial images $M_0$; and
- fitting of tissue properties (or spectral properties thereof) indicated in the model AM for different regions of the body anatomy therein, and spectral data of corresponding voxels/pixels in the in the initial images $M_0$.

For example, in some embodiments the mapping is determined based on the fitting of the tissue properties while minimizing a model morphing required to achieve such fitting to the positions in the initial images.

Alternatively, or additionally, as indicated above, in some embodiments the model AM is or may include an ML model trained for recognizing/classifying the anatomical structure of interest within images (e.g., the initial image(s) $M_0$) of a patient's body and determining/estimating the ROI occupied by the anatomical structure therein the images. In such embodiments the operation 230 may include operating the ML model on the grabbed initial image(s) $M_0$ to thereby yield data indicative of the ROI (shape/size/location thereof) within the FOR apparent in the initial image(s) $M_0$.

As will be appreciated, once the ROI is identified within the initial image(s) $M_0$, the location of the ROI relative to the body coordinates may also be determined (considering that the initial images are grabbed together with position data of the imaging device 50 relative to the patient's body, as obtained by the position sensor 52).

Accordingly, in operation 240, which may be carried out by the acquisition utility 116 after the ROI is determined, the system 100 utilizes the properties of the determined ROI (its shape, location and/or size relative to the body coordinates), as well as optionally the current position of the imaging device 50 (as obtained from the position sensor 52) to set-up/adjust/optimize suitable capturing parameters for the imaging device 50 for capturing substantially segregated images of the ROI by the imaging device 50. In other words, the capturing parameters are adjusted such that the region CR being captured by the imaging device is contracted/adjusted to cover the ROI substantially exclusively (i.e., with minimal margins as far as permitted by the adjustment of the capturing parameters) such that operating the imaging device 50 with the adjusted capturing parameters yields acquisition of a substantially segregated image of the anatomic structure of interest. Particularly the adjustment of the capturing parameters may include adjustments of parameters affecting the FOV angle of the imaging device 50, e.g. such that the captured FOV substantially matches the angular extent of the ROI relative to the imaging device 50; and/or adjustment of the DOF for the imaging device (e.g. the range of distances from the imaging device 50 which captured with acceptable resolution), such that it fits/matches as closely as possible to the depth extent of the ROI.

Depending on the imaging device's type/technology, the capturing parameters being adjusted may include one or more of the capturing parameters described in the following:

- Adjustment of parameters affecting the imaging device's FOV which may include for instance any one or more of the following:
  - adjusting the scanning angle of the imaging device (applicable in cases where the imaging device operates in scanning mode).; and/or
  - adjusting the zoom properties of the imaging device's "optic" e.g., in case the imaging device is equipped with optics and that the optics facilitates zooming. In this regards it should be understood that the term optics is used to designate any type of elements that can manipulate the fields/waves of the type sensed/imaged by the imaging device 50 (e.g. pertaining not necessarily to elements that manipulate light fields, but also alternatively or additionally to elements other type(s) of fields image by the imaging device such as acoustic lenses or meta materials structures capable of manipulating (refracting/diffracting) sound, ultrasound or electromagnetic fields).
  - Adjusting the angle of active illumination (which is applicable in cases where the imaging device employs such illumination).

To this end in some embodiments the parameters affecting the imaging device's FOV field of view are adjusted such that the FOV of the imaging device is contracted substantially closer to the ROI at which the anatomical structure of interest resides in order to suppress capturing of voxels located from the sides of the ROI. Accordingly, the lateral extent of the region CR being captured by the imaging device is fitted more closely to the lateral extent of the ROI.

Alternatively, or additionally, adjustment of parameters affecting the imaging device's DOF, which may include for instance any one or more of the following:

- in imaging devices having active illumination, such as ultrasound imaging devices, adjusting the gating time interval between the timings of the active illumination (e.g., pulses) and the timings of the sensor's operation to grab the returned signals (echoes/reflections) in order to thereby adjust the effective range of distances from which the sensor's accepts/senses returning echoes/reflection, thereby limiting the DOF to this range of.
- in imaging devices having active illumination, adjusting the frequency (ies) of the active illumination in order to affect/control the penetration depth of the active illumination and thereby adjust the DOF captured by the imaging device. Indeed, as will be appreciated by those versed in the art of for example ultrasound imaging, utilizing Active illumination with lower ultrasound frequencies yield higher penetration depth of the illumination (e.g. sound) thereby facilitating of more remote anatomical structures and/or with greater DOF. Conversely, with higher frequency closer structure are captured with higher resolution while more remote structures are diminished from the image (as the active illumination does not reach them with sufficient intensity). In some embodiments the sensor's response to frequencies of the returned echoes/reflections (e.g., or the filtering of such frequencies) may alternatively or additionally also be adjusted in order to achieve some similar effects.

adjusting a gain of said imaging device and/or an active illumination intensity thereof, according to at least one of a location/distance of the ROI to the imaging device, and/or according to tissue types included in the anatomical structure of interest (e.g. as may be indicated by the model AM). As will be appreciated by those versed in the art of imaging, such manipulations in the sensors gain and/or active illumination intensity may affect the dynamic range of the sensor thereby directly or indirectly affecting the range of distances from which image details are captured by the sensor;

in imaging devices such as scanning imaging devices in which beamforming technology is used, the focal points of the beamformed active illumination, or beamformed returned echoes/reflections, may be adjusted to the be whiting the distance range of the desired DOF, to thereby suppress sensing of returns/echoes from distances outside that range.

in imaging devices such as staring/snapshot imaging devices having an adjustable aperture, the size of the aperture's opening may be adjusted to yield images of wider or narrower depths of focus (i.e., using smaller or larger aperture respectively) thereby adjusting the range of distances from which the imaged details appear sharp in the image and blurring (thereby suppressing) imaged details outside that range.

Thus, in some embodiments the parameters affecting the imaging device's depth of field DOF are adjusted such that the DOF of the imaging device is contracted in the depth direction to fit substantially closer to the ROI at which the anatomical structure of interest resides, thereby suppress capturing of voxels located in-front or behind the ROI. To this end, the by adjusting the FOV and/or DOF in the manner described above the capturing region CR of the imaging device 50 is adjusted to fit/match the ROI with no or only small margins.

In this connection, with reference to FIG. 3C, it should be noted that in some implementations the margins between the capturing region CR of the ROI may be further minimalized by individual adjustment of the DOF parameters per each subset of FOV angles being captured (e.g., such that the DOF is individually fitted to the actual depth extent of the ROI at each such subsets of FOV angles. Indeed, for example in imaging devices that operate in scanning mode, the system 100 may apply different adjustment of the DOF parameters different scan angles. FIG. 3C illustrated this case for example, and shows in self-explanatory manner the catheter 21, similar to that illustrated in FIG. 3A, with the capturing region CR of the imaging device 50 fitted/contracted in this manner. As illustrated, in this example the DOF captured by the imaging device is adjusted/varied across the scanning angles of the imaging device along the FOV such that different sections of the FOV are imaged with different DOFs: illustrated for example $DOF_1$, $DOF_k$ and $DOF_n$ in the figure. Accordingly, the shape of the capturing region CR is fitted more closely to the shape of the ROI at which the anatomical structure of interest resides, optionally with reduce margins as compared to the case the DOF parameters are adjusted globally for the entire FOV.

It should be noted that in some embodiments additional capturing parameters may be adjusted in order to yield higher quality segregated image of the ROI. For instance in some embodiments where the shape of the anatomical structure of interest is variable, for example when capturing a beating heart or portion thereof, the system 100 may be adapted to also adjusting the frame rate (e.g. scanning rate/shutter's speed) of the imaging, whereby imaging with high shutter/scanning rate permits imaging of anatomical structures which are in motion during the imaging, while lower frame rate may facilitate images with improved signal to noise ratio (SNR).

Further, in operation 240, after setting up the suited capturing parameters, the system 100 (e.g., the acquisition utility 116 thereof) operates the imaging device 50 to capture images $M_R$ of the ROI by using said capturing parameters, thereby obtain the volumetric segregated image $M_R$ of the anatomical structure of interest.

In optional operation 250, the volumetric segregated image may then be further processed/rendered (e.g., by a rendering utility 118 of the system 100), to facilitating presentations of anatomical structure present in said volumetric segregated image $M_R$ from various angels/points of view and/or various 2D slices thereof, and display of the same to the operator/physician 30 (e.g., via the UI 115).

As indicated above in some cases, the volumetric segregated image $M_R$ presents the region of interest occupied by the anatomic structures with some remaining margins that could not be entirely suppressed/removed by the adjustment of the capturing parameters. Therefore, in some embodiments of the present invention the system 100 (e.g., the rendering utility 118 thereof) may be adapted to further process the segregated image $M_R$ in order to substantially remove any remaining margins which may appear therein in the surroundings of the anatomical structure there, and yield a cropped image $M_C$ of the anatomical structure without said margins. To Achieve that according to some embodiments of the present invention the one or more processors 110 of the system are may be configured to process the volumetric image $M_R$ obtained from the imaging device 50 (or 2D/3D images rendered therefrom) by using the model AM of the anatomical structure of interest, to identify voxels in these image(s) which are not associated with the anatomical structure of interest and removing/blanking said voxels. For instance, in case the model AM is a morphological model as described above, such processing may include determining a map between one or more regions (voxels) of the at least portion of the body anatomy present in the model AM and corresponding voxels in the at least one volumetric image $M_R$ and utilizing the map to crop the image $M_C$ in which only the voxels of which are mapped to the model AM remain un-blanked. In case the model AM is a trained ML model, such cropping procedure may be applied providing the image as input to the model for receiving therefrom as output data indicative of the voxels that are associated with the anatomical structure (e.g., in a manner similar to the model processing described in relation to operation 230 above). The operations of the system 100 and/or the rendering utility 118 thereof, which may be incorporated with this embodiment of the invention for rendering cropped images of the anatomical structure of interest, are described in more details below with reference to the embodiments of FIGS. 4A and 4B.

In some embodiments the system 100 is adapted to produce a video of the portion of the body anatomy of interest, segregated/cropped from the tissues or other fluids surrounding it.

To achieved that, in such embodiments the system 100 is adapted to operate the one or more processors 110 whose functions are described above, in order to generate a plurality of successive segregated/cropped images $M_R/M_C$ of the portion of the body anatomy of interest, for a plurality of respectively successive time frames, and to render the plurality of successive segregated/cropped $M_R/M_C$ images from at least one desired angle of view or from a plurality of angles of view continuously varied along a span of said time frames, and thereby obtain a video of the body anatomy of interest cleared from tissues not associated therewith.

In this regard it should be noted that according to some embodiments the system 100 may be configured and operable to adjust the capturing parameters of the imaging device and grab images/video of the ROI in real time and gram thus enabling real-time capture of segregated images/video of the anatomical structure of interest. For instance those two actions of imaging device parameter adjustment (according to the position of the catheter relative to the ROI) and corresponding image capturing may be carried out in real time (as an ongoing real time loop) so that the images are acquired and optimized for real-time rendering of the anatomical structure of interest in a segregated manner (i.e. with its surrounding diminished in the captured/rendered images/video).

As indicated above embodiments of the present invention may be implemented with catheters' such as 21 in which various types of imaging devices 50 may be installed. For instance, the imaging device 50 may be an ultrasound imaging device, and/or an imaging device capable of imaging electromagnetic radiation/fields in the optical regime and/or in other electromagnetic regimes. Nonetheless it should be noted that the invention is particularly advantageous for use with imaging devices such as ultrasound imaging devices, that can be operated in situ and in vivo within a patient's body for imaging internal organs thereof. Additionally, advantageously imaging devices utilizing active illumination (such as in most ultrasound imaging devices) and/or imaging devices utilizing scanning technology (as opposed to imaging devices operating in snapshot mode) may provide enhanced control over the properties of the region being captured CR thereby (e.g. in terms of its DOF and/FOV), thereby facilitating capture of high quality segregated images of an anatomical structure of interest, by proper adjustment of their active illumination scheme/gating, and/or their operation during scanning of different scan sections.

Figure 4A:
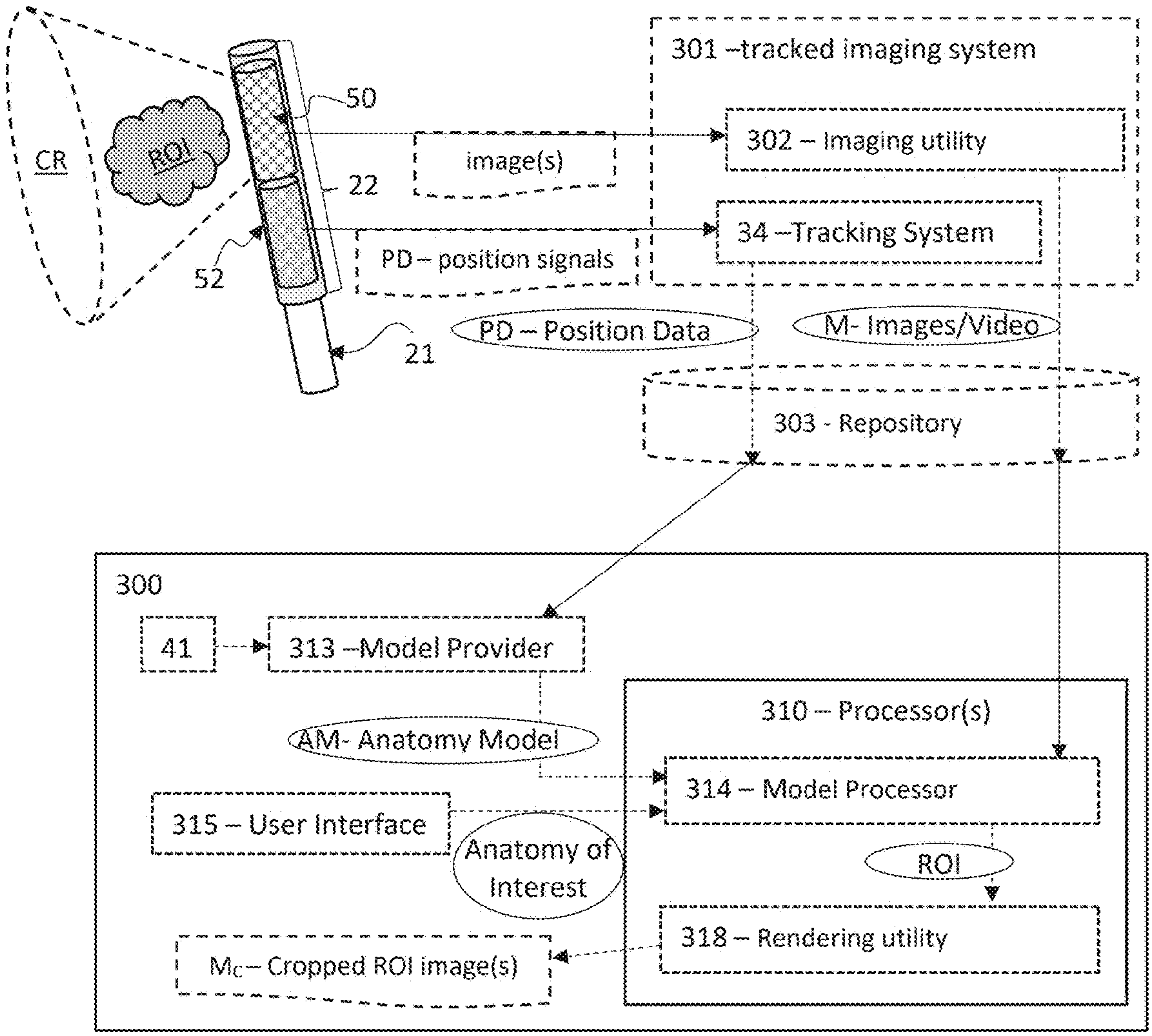
FIGS. 4A and 4B are respectively a block diagram and a flowchart presenting a system and a method for cropping medical images of a body anatomy of interest according to embodiments of the present invention.
Figure 4B:
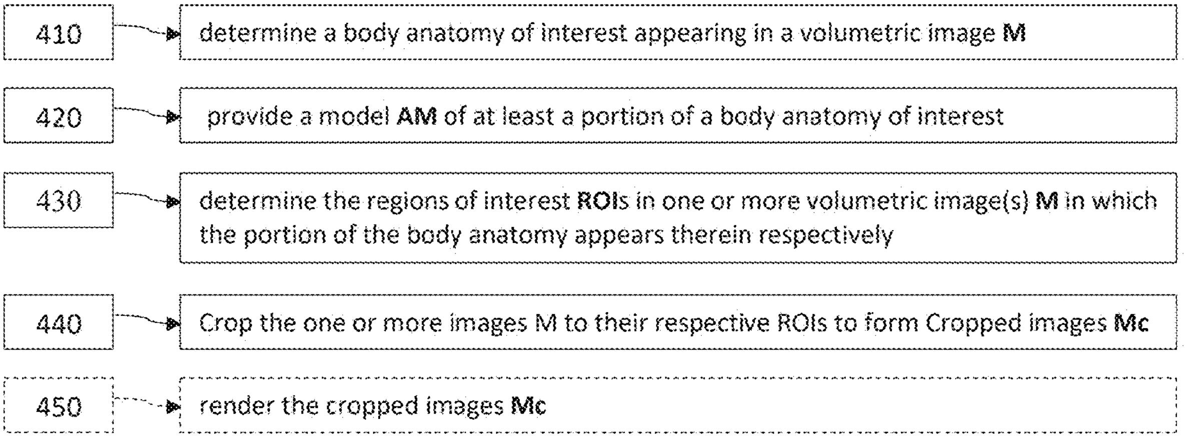

Reference is now made together to FIGS. 4A and 4B in which a system 300 and method 400 according to another embodiment of the present invention for producing images of anatomical structures are schematically illustrated. The system 300 is adapted to process images M (e.g. volumetric or 3D images, or video sequence(s) thereof) obtained from within a patient's body in which an anatomical structure of interest or part thereof appears, together with position data PD and to identify/recognize the region of interest (ROI) within the images M at which the anatomical structure of interest appears, and crop the images M to the ROI to form cropped images $M_C$ in which the anatomical structure of interest separated/cleared from other tissues in its surrounding (e.g. 2D, 3D or volumetric cropped images, or cropped video sequence(s) thereof).

The system 300 is connectable directly or indirectly for receiving image data M and corresponding position data PD of images captured by a catheter 21 similar to that illustrated and described above. To this end, the system 300 may be connected to a tracked imaging system 301 and/or to a data repository 303 for receiving therefrom such image data M and corresponding position data PD.

For instance, the tracked imaging system 301 may be similar as described above and may be connectable to the catheter 21 which has a distal tip 40 furnished with an imaging device 50 capable of capturing volumetric images within a patient's 28 body, and a position sensor 52 capable of providing position data indicative of a position of the imaging device 50). The tracked imaging system 301 may for instance include an imaging utility 302 adapted for obtaining images M captured by the imaging device 50 of the catheter 21, and a positioning system 34 which is capable of processing position signals from the position sensor 52 of the catheter 21 and optionally to receive capturing parameters by which the imaging device 50 is operated for capturing the images M to determine position data PD indicative of the position of the imaging device 50 from which the images M are respectively captured relative to the patient's body (e.g. the position data PD may include data indicative of the imaging device's FOR which may be based primarily on the imaging device's position, and/or data indicative of the region CR being captured by the image(s) M which may be based also on the capturing parameters by which the image(s) are acquired).

In some embodiments, the tracked imaging system 301 may be connected directly to the system 300 for providing the images M and corresponding position data PD thereto. Alternatively, or additionally, in some embodiments the tracked imaging system 301 is connectable to data repository 303 (e.g., a data storage or data base) and is adapted to store the images M and the corresponding position data PD therein, to enable their further processing by the system 300.

In turn, the system 300 is adapted to receive/obtain the images M and corresponding position data PD either directly from system 301 or indirectly from the repository 303, and to process/render the images M based on the position data PD to yield cropped images $M_C$ of an anatomical structure/body-anatomy of interest appearing therein. The system 300 includes one or more processors 310 adapted to carry out the following:

- Obtain (e.g., by a model processor 314) a model AM of the anatomical structure of interest which appears in the image(s) M and process the images utilizing the model AM in order to determine a region of interest (ROI—being used in the context of FIGS. 4A and 4B to designate a subset of image voxels/pixels) which is occupied by the body anatomy of interest and to which the image(s) should be cropped; and
- Render (e.g., by rendered utility 318) the images M based on the identified ROI to crop the images to the ROI and thereby produce cropped images $M_C$ of the anatomical structure/body-anatomy of interest.

To this end, the system 300 typically includes or is associated with a model provider 313 (e.g., a repository of anatomical models) capable of providing models of various body anatomies which might be of interest for cropping images thereto. The model provider may be for example similar to the model provider 113 described above with reference to FIGS. 3A and 3B and may be adapted to provide morphological models and/or machine learning models of the various body anatomies, which may be generic or patient specific models, as described above. To this end, for brevity, descriptions of these types of anatomical models AM(s), their contents/use and/or operation will not be repeated here in details, except for clarifying that their configuration/content may be similar to the models described above in detail.

In some embodiments the system 300 is optionally also associated with a user interface utility 315, similar to interface utility 115 that described above, enabling a physician and/or an operator of the system 300 to view the content of the images M and selecting/marking of the anatomical structure(s) of interest (or portions thereof) appearing therein, to instruct the system 300 to crop the image(s) M to the selected anatomical structure (or to the selected portions thereof). For brevity, detailed description of the user interface utility 315 will not be repeated here, as it would be appreciated that the description of the interface utility 115 above applies also to the user interface utility 315 of this embodiment.

In the following the configuration and operation of the system 300 will be further described in mode details with reference to the method 400 illustrated in FIG. 4B, which is implemented by the system 300.

In operation 410 at least one initial image $M_0$ and its respective position data PD is obtained by the system 300, and an anatomical structure of interest, or portion thereof, which appears in the image M, is identified. In some embodiments the identification of the anatomical structure of interest is performed automatically based on the provision data PD of the image, which is indicative of the location from which the image M is grabbed within the patient's body and optionally other capturing parameters of the image, and on predetermined knowledgebase data indicative of anatomical structure(s) expected/known to appearing in such location. Alternatively, or additionally, in some embodiments, in order to identify the portion of the body anatomy of interest more precisely, operation 410 may include presenting the grabbed image M to a physician/operator 30 for instance in similar manner as described above via user interface 315, and responsive to said presentation, obtaining from the physician/operator input data selection/markings indicative of a selected region of interest ROI or of a specific anatomical structure appearing within the image M.

Based on the identified anatomical-structure/body-anatomy of interest, which is done either automatically or via user selection, in operation 420 a model AM of at least a portion of the body anatomy of interest is retrieved, e.g., by the model provider 313 of system 300.

As indicated above, in various embodiments of the invention the model AM may include, or is constituted by, a morphological model of the anatomical structure(s) of interest, indicative of at least one of its shape, size and optionally also its typical position, as described above. The morphological model AM may be generic or patient-specific model (e.g. in the latter case the model maybe one acquired by the use of a mapping medical device 41 associated with the system 300, in the manner described above with reference to FIGS. 3A and 3B). In some embodiments the morphological model AM also further includes tissue data including for instance of spectral information indicative of the appearance of various tissues of the anatomical structure of interest in images thereof.

Alternatively, or additionally the model AM, which is retrieved by the model provider 313 may include or be constituted by a machine learning (ML) model trained for processing/recognition of the anatomical structure of interest within images M in which it appears. As will be appreciated by those versed in the art, such an ML model may be similar to the ML model described above with reference to FIGS. 3A and 3B In operation 430 (e.g., which may be for instance performed by the model processor 314) the anatomical model AM is applied to one or more images M in which the anatomical structure of interest appears, to identify in those images respectively, the regions of interest ROI therein (e.g., the groups of pixels/voxels thereof) in which the anatomical structure of interest appears.

In this connection it should be noted that the operation 430 may be carried out in similar manner as the operation 230 described above in details with reference to FIGS. 3A and 3B, only that here it is being applied in order to identify the ROIs within the grabbed images M themselves. In this regard, in embodiments/cases where the model AM is a morphological model, the respective ROIs in the images may be determined by fitting the model to the contents of the images $M_0$ (e.g. in a manager similar to that described above with respect to the fitting/mapping of the model AM to the initial $M_0$ in FIG. 3A). Alternatively, or additionally in embodiments/cases where the model AM is a machine learning (ML) model, the model AM may be operated-on (fed-with) each of the images M to thereby yield data indicative of the respective ROIs in those images at which the body anatomy of interest appears.

In operation 440 (e.g. which may be carried out by rendering utility 318), the one or more images M may be optimized by modifying volumetric characteristics such as Gamma, Brightness, Sharpness, and cropped to their respective ROIs identified in operation 430. As will be appreciated by those versed in the art, cropping may be performed by blanking/removing pixels/voxels of in those images which are not part of the ROI. Accordingly, cropped images $M_c$ are obtained in which the anatomical structure/body-anatomy of interest appears without (cleared of) the tissues or other features surrounding it.

Further, in optional operation 450 the system 300 (e.g., rendering utility 318) may render the cropped images to yield desired 2D, 3D and or video presentations of the cropped anatomical structure of interest appearing from various angels/points of view and/or various 2D slices thereof, and display of the same to the operator/physician 30 (e.g., via the UI 115).

To this end, as indicated above, the grabbed images M being processed by the system 300, and from which the cropped images are obtained, may themselves be 2D, 3D/volumetric images or video sequences thereof. Thus, in case the images M and/or their cropped versions $M_c$ are 3D/volumetric images, operation 450 may be carried out for rendering desired 2D slices of those cropped images. Alternatively, or additionally, the operation 450 may be carried out for rendering the 3D/volumetric images from desired point of view. Yet additionally or alternatively, the operation 450 may be carried out for constructing video sequences of the anatomical structure of interest from these cropped images, whereby the video sequences may present 3D video of the anatomical structure of interest separated from the tissues surrounding it, or a 2D video presenting 2D slices/views thereof separated from it surrounding. After knowing the invention, person of ordinary skill in the art will readily appreciate the various rendering options that may be implemented by method operation 450 for rendering the anatomical structure appearing in the cropped images $M_c$ to form 2D, 3D or video thereof presented from various angles of view or presenting various slices thereof.

EXAMPLES

Example 1. A system to generate images of anatomical structures, the system is connectable to a catheter having a distal tip furnished with an ultrasound imaging device capable of capturing volumetric images and a position sensor capable of providing position data indicative of a position of the imaging device. The system includes one or more processors configured and operable to carry out the following:

process the position data of the ultrasound imaging device to determine a volumetric field of regard (FOR) of said imaging device relative to a patient's body;

provide a model indicative of at least a portion of a body anatomy present in the patient's body within said FOR;

adjust capturing parameters of said ultrasound imaging device based on said model, to optimize capturing of said at least portion of the body anatomy by the ultrasound imaging device with diminished appearance of its surrounding tissues.

Example 2. The system according to example 1, wherein the capturing parameters of the ultrasound imaging device are adjusted based on the model in order to yield an optimized capturing of one or more segregated volumetric image of the at least portion of the body anatomy, in which the appearance surrounding tissues is diminished; and wherein the system obtains said one or more volumetric segregated images and produces therefrom at least one of: a 2D segregated image, a 3D segregated image and a video sequence of 2D or 3D segregated images, of the at least portion of the body anatomy in which appearance of the surrounding tissues is diminished.

Example 3. The system according to example 1 or 2, wherein the ultrasound imaging device is capable of capturing volumetric images of the patient's body with up to a certain maximal field of view and maximal depth of field extents; the one or more processors are adapted to process the position data of the ultrasound imaging device to determine a registration between the certain maximal field of view and maximal depth of field extents and the patient's body and thereby determine the volumetric FOR of the imaging device relative to the patient's body.

Example 4. The system according to any one of examples 1 to 3, wherein the system includes a user interface adapted to receive input data indicative of the at least portion of the body anatomy to be captured by the ultrasound imaging device.

Example 5. The system according to any one of examples 1 to 4, wherein the adjustment of the capturing parameters of the ultrasound imaging device based on the model, includes utilizing the model to determine a region of interest (ROI) at which said at least portion of the body anatomy is present within the FOR of the ultrasound imaging device.

Example 6. The system according to example 5, wherein said utilizing the model to determine the region of interest (ROI) includes operating the ultrasound imaging device to obtain at least one initial image of at least part of said FOR and determining an association between pixels/voxels in the at least one initial image and at least portion of the body anatomy modeled by said model.

Example 7. The system according to any one of examples 1 to 6, wherein the model includes a morphological model indicative of at least one of a shape, size and position of the at least portion of the body anatomy.

Example 8. The system according to example 7, wherein the morphological model includes at least one of the following:

a generic model indicative of at least one of a characteristic shape, characteristic size and characteristic position of the at least portion of the body anatomy;

a patient specific model indicative of at least one of a shape, size and position of the at least portion of the body anatomy of the patient's body;

a pathology specific model indicative of at least one of a shape, size and position of the at least portion of the body anatomy having a certain pathology condition;

data indicative of one or more properties of one or more tissue types present in the at least portion of the body anatomy.

Example 9. The system according to any one of examples 6 to 8, wherein the association is determined based on a combination of one or more of the following:

determining a fit between the positions of different regions of the body anatomy in the morphological model and corresponding pixels/voxels of the initial image; and determining a fit between tissue properties indicated in the model for different regions of the body anatomy, and spectral data of the corresponding pixels/voxels.

Example 10. The system according to any one of examples 6 to 9, wherein the model includes a machine learning model trained for recognition of the body anatomy within images in which the body anatomy appears; and wherein said association is determined by employment of the model to recognize said body anatomy within the initial image.

Example 11. The system according to any one of examples 6 to 10, wherein the adjustment of the capturing parameters includes adjusting one or more of the following capturing parameters of the ultrasound imaging device to optimize capturing of a region of interest (ROI) in the FOR that is occupied by the at least portion of the body anatomy:

adjusting a field of view (FOV) of the ultrasound imaging device by which to conduct the capturing in order to suppress capturing of regions located from the sides of the at least portion of the body anatomy;

adjusting a depth of field (DOF) of the ultrasound imaging device in order to suppress capturing of regions located in front and/or behind the body anatomy relative to the ultrasound imaging device;

adjusting at least one of a gain of the ultrasound imaging device and an active illumination intensity thereof, according to at least one of: a location or distance of the body anatomy relative to the ultrasound imaging device, and tissue types included in the body anatomy;

adjusting a frequency of an active illumination of the ultrasound imaging device to thereby control a penetration depth of the active illumination (penetration of the illumination through body tissues), according to a location of the body anatomy relative to the imaging device;

adjusting gating times between the active illumination and image sensing by the ultrasound imaging device to control a span(s) of the DOF relative to the imaging device according to a location of the body anatomy relative to the ultrasound imaging device; and adjusting a frame/scan rate of the ultrasound imaging device in accordance with movement characteristics of the body anatomy to accommodate accurate capturing of anatomies in motion.

Example 12. The system according to any one of examples 2 to 11, wherein the one or more processors are further adapted to crop, based on the model, at least one of image of: the volumetric segregated images, 2D segregated image, 3D segregated image and the video sequence of 2D or 3D segregated images; and wherein cropping the at least one of image includes utilizing the model to determine association between voxels or pixels of the image and the at least portion of the body anatomy, and removing or blanking voxels or pixels of the at least one of image which are not associated with the at least portion of the body anatomy, thereby obtaining at least one cropped image of the body anatomy, in which pixels or voxels not associated with said body anatomy are removed or diminished.

Example 13. The system according to any one of examples 2 to 12, wherein the system includes at least one medical device having a position sensor thereon and being suited for mapping the at least portion of the body anatomy of the patient's body; and wherein the one or more processors are adapted to track positions of the at least one medical device, and recording the tracked positions associated with the body anatomy to thereby construct a patient specific morphological model of the at least portion of the patient's body anatomy.

Example 14. The system according to example 13, wherein at least one of the following:

- the patient specific morphological model includes a cloud of points formed by the recorded tracked positions and indicative of a shape of the at least portion of the patient's body anatomy;
- the medical device includes one or more sensors adapted to sense one or more tissues properties of the at least portion of the patient's body anatomy at the tracked positions.

Example 15. The system according to and one of examples 2 to 14, being adapted to produce a video of the at least portion of the body anatomy segregated from surrounding tissue; and wherein production of the video includes operating the one or more processors to process a plurality of volumetric images obtained during successive time frames to generate therefrom a plurality or corresponding segregated or further cropped images being 2D or 3D images and thereby obtaining a video sequence of 2D or 3D images of the at least portion of the body anatomy of the patient's body substantially cleared from body tissues not associated with the body anatomy.

Example 16. A method to generate images of anatomical structures, the method includes:

- obtaining position data from a catheter having a distal tip furnished with an ultrasound imaging device capable of capturing volumetric images, and a position sensor providing said position data such that it is indicative of a position of said ultrasound imaging device;
- processing the position data to determine a volumetric field of regard (FOR) of the ultrasound imaging device relative to a patient's body;
- providing a model indicative of at least a portion of a body anatomy present in the patient's body within the FOR; and
- adjusting capturing parameters of the ultrasound imaging device based on the model, to optimize capturing of the at least portion of the body anatomy by the ultrasound imaging device with diminished appearance of its surrounding tissues.

Example 17. The method according to example 16, further including: obtaining at least one volumetric segregated image captured by the ultrasound imaging device with the capturing parameters being adjusted such that the at least portion of the body anatomy appears therein substantially segregated from body tissues not associated with the at least portion of the body anatomy; and processing the at least one volumetric segregated image to yield at least one of: a 2D segregated image, a 3D segregated image, and a video sequence of 2D or 3D segregated images, of the at least portion of the body anatomy.

Example 18. The method according to any one of examples 16 or 17, wherein the ultrasound imaging device is capable of capturing volumetric images of the patient's body with up to a certain maximal field of view and maximal depth of field extents; the method includes processing the position data of the imaging device to determine a registration between the certain maximal field of view and maximal depth of field extents and the patient's body and thereby determine the volumetric FOR of the imaging device relative to the patient's body.

Example 19. The method according to any one of examples 16 or 18, wherein the method includes receiving, from a user interface, input data indicative of the at least portion of the body anatomy to be captured by the ultrasound imaging device.

Example 20. The method according to any one of examples 16 or 19, wherein the adjustment of the capturing parameters of the ultrasound imaging device based on the model includes utilizing the model to determine a region of interest (ROI) at which the at least portion of the body anatomy is present within the FOR of the imaging device.

Example 21. The method according to example 20, wherein said utilizing of the model to determine the region of interest (ROI) includes operating the ultrasound imaging device to obtain at least one initial image of at least part of the FOR and determining an association between pixels/voxels in the at least one initial image and at least portion of the body anatomy modeled by the model.

Example 22. The method according to example 21, wherein the model includes at least one of the following:

- a morphological model indicative of at least one of a shape, size and position of the at least portion of the body anatomy; and wherein said association is determined based on a fit between the positions of different regions of the body anatomy in the morphological model and corresponding pixels/voxels of the initial image; and
- a machine learning model trained for recognition of the body anatomy within images in which the body anatomy appears; and wherein said association is determined by employment of the model to recognize the body anatomy within the initial image.

Example 23. The method according to any one of examples 16 to 22, wherein the adjustment of the capturing parameters includes adjusting one or more of the following capturing parameters of the imaging device to optimize capturing of a region of interest (ROI) in the FOR that is occupied by the at least portion of the body anatomy:

adjusting a field of view (FOV) of the imaging device by which to conduct the capturing in order to suppress capturing of regions located from the sides of the at least portion of the body anatomy;

adjusting a depth of field (DOF) of the imaging device in order to suppress capturing of regions located in front and/or behind the body anatomy relative to the imaging device;

adjusting at least one of a gain of the imaging device and an active illumination intensity thereof, according to at least one of: a location or distance of the body anatomy relative to the imaging device, and tissue types included in the body anatomy;

adjusting a frequency of an active illumination used by the imaging device to thereby control a penetration depth of the active illumination according to a location of the body anatomy relative to the imaging device;

adjusting gating times between the active illumination and image sensing by the imaging device to control a span(s) of the DOF relative to the imaging device according to a location of the body anatomy relative to the imaging device; and adjusting a frame/scan rate of the imaging device in accordance with movement characteristics of the body anatomy to accommodate accurate capturing anatomies in motion.

Example 24. The method according to any one of examples 17 to 23, wherein the method further includes cropping at least one of image of the volumetric segregated image, 2D segregated image, 3D segregated image and the video sequence of 2D or 3D segregated images, based on the model; and wherein the cropping of the at least one of image includes utilizing the model to determine association between voxels or pixels of the image and the at least portion of the body anatomy, and removing or blanking the voxels or pixels of the at least one of image not associated with the at least portion of the body anatomy to yield at least one cropped image of the body anatomy in which pixels or voxels not associated with the body anatomy are removed or diminished.

Example 25. The method according to any one of examples 16 to 24, wherein the method further includes constructing a patient specific morphological model of the at least portion of the patient's body anatomy; whereby the constructing includes tracking the positions of at least one medical device having a position sensor thereon and being suited for mapping the at least portion of the body anatomy of the patient; and recording the tracked positions of the medical device at positions associated with the body anatomy to thereby construct the patient specific morphological model with a cloud points of the at least portion of the patient's body anatomy.

Example 25. A system to produce images of anatomical structures. The system is adapted for receiving images captured by a catheter having a distal tip furnished with an imaging device capable of capturing images from within a patient's body, and a position sensor capable of providing position data indicative of a position of the imaging device. The system includes one or more processors adapted to carry out the following:

obtaining at least one image captured by the imaging device and the position data indicative of the position of the imaging device within the patient's body when the at least one image is acquired;

utilizing the position data to determine a region captured by the at least one image relative to the patient's body and determining at least a portion of a body anatomy of interest present in the captured region;

providing a model of the body anatomy; and cropping the at least one of image based on the model whereby the cropping includes utilizing the model to determine association between voxels or pixels of the image and the at least portion of the body anatomy, and removing or blanking the voxels or pixels of the at least one of image which are not associated with the at least portion of the body anatomy to yield at least one cropped image of the body anatomy from which pixels or voxels not associated with the body anatomy are removed or diminished.

Example 26. The system according to example 25, wherein at least one of the following:

the imaging device includes an ultrasound imaging device; and the imaging device is adapted for capturing volumetric images from within the patient's body; and the at least one image is a volumetric image captured thereby.

Example 27. The system according to any one of examples 25 or 26, wherein the system includes a user interface adapted to receive input data indicative of at least a portion of the body anatomy to be presented in the cropped image.

Example 28. The system according to any one of examples 25 to 27, wherein the model includes a morphological model indicative of at least one of a shape, size and position of the at least portion of the body anatomy.

Example 29. The system according to example 28, wherein the morphological model includes at least one of the following:

a generic model indicative of at least one of a characteristic shape, characteristic size and characteristic position of the at least portion of the body anatomy;

a patient specific model indicative of at least one of a shape, size and position of the at least portion of the body anatomy of the patient's body; and the morphological model includes data indicative of one or more properties of one or more tissue types present in the at least portion of the body anatomy.

Example 30. The system according to example 29, wherein the association between the voxels or pixels of the at least one image and the at least portion of the body anatomy is determined based on a combination of one or more of the following:

determining a fit between the positions of different regions of the body anatomy in the model to corresponding voxels of the at least one image; and determining a fit between tissue properties indicated in the model for different regions of the body anatomy, to spectral data of the corresponding voxels.

Example 31. The system according to any one of examples 25 to 30, wherein the model includes a machine learning model trained for recognition of the body anatomy within images in which the body anatomy appears; and said association is determined by employment of the model to recognize the body anatomy within the at least one image.

Example 32. The system according to any one of examples 25 to 31 being adapted to produce a cropped video of the at least portion of the body anatomy from which pixels/voxels presenting tissues surrounding the at least portion of the body anatomy are blanked or removed; and wherein production of the video includes operating the one or more processors to process a plurality of images obtain during successive time frames to generate therefrom a video sequence including a corresponding plurality of cropped images presenting the at least portion of the body anatomy of the patient's substantially cleared from body tissues not associated therewith.

Example 33. The system according to any one of example 32, wherein the images are 3D/volumetric images and the wherein the one or more processors are adapted to produce a cropped 3D/volumetric video presenting the at least portion of the body anatomy.

Example 34. A method to produce images of anatomical structures, the method includes:

- obtaining at least one image captured by a catheter having a distal tip furnished with an imaging device capable of capturing images from within a patient's body and a position sensor capable of providing position data indicative of a position of the imaging device;
- obtaining position data indicative of the position of the imaging device within the patient's body when the at least one image is captured;
- utilizing the position data to determine a region captured by the at least one image relative to the patient's body;
- determining at least a portion of a body anatomy of interest present in the captured region;
- providing a model of the body anatomy; and
- cropping the at least one of image based on the model whereby the cropping includes utilizing the model to determine association between voxels or pixels of the at least one image and the at least portion of the body anatomy, and removing or blanking the voxels or pixels of the at least one of image which are not associated with the at least portion of the body anatomy to yield at least one cropped image of the body anatomy from which pixels or voxels not associated with the body anatomy are removed or diminished.

Example 35. The method according to example 34, wherein at least one of the following:

- the imaging device includes an ultrasound imaging device; and
- the imaging device is adapted for capturing volumetric images from within the patient's body; and the at least one image is a volumetric image captured thereby.

Example 36. The method according to example 34 or 35, wherein the method includes receiving, from a user interface, input data indicative of the at least portion of the body anatomy to be presented in the cropped image.

Example 37. The method according to any one of examples 34 to 36, wherein the model includes a morphological model indicative of at least one of a shape, size and position of the at least portion of the body anatomy.

Example 38. The method according to example 37, wherein the morphological model includes at least one of the following:

- a generic model indicative of at least one of a characteristic shape, characteristic size and characteristic position of the at least portion of the body anatomy;
- a patient specific model indicative of at least one of a shape, size and position of the at least portion of the body anatomy of the patient's body; and
- the morphological model includes data indicative of one or more properties of one or more tissue types present in the at least portion of the body anatomy.

Example 39. The method according to example 38, wherein the association between the voxels or pixels of the at least one image and the at least portion of the body anatomy is determined based on a combination of one or more of the following:

- determining a fit between the positions of different regions of the body anatomy in the model to corresponding voxels of the at least one image; and
- determining a fit between tissue properties indicated in the model for different regions of the body anatomy, to spectral data of the corresponding voxels.

Example 40. The method according to any one of examples 34 to 39, wherein the model includes a machine learning model trained for recognition of the body anatomy within images in which the body anatomy appears; and wherein said association is determined by employment of the model to recognize the body anatomy within the at least one image.

Example 41. The method according to any one of examples 34 to 40, wherein the method includes producing a cropped video of the at least portion of the body anatomy from which pixels/voxels presenting tissues surrounding the at least portion of the body anatomy are blanked or removed. The production of the video includes processing a plurality of images captured during successive time frames by the imaging device to generate therefrom a video sequence including a corresponding plurality of cropped images presenting the at least portion of the body anatomy of the patient's substantially cleared from body tissues not associated therewith.

Example 42. The method according to examples 40, wherein the images are 3D/volumetric images and wherein the method is adapted to produce the cropped video as a 3D/volumetric video presenting the at least portion of the body anatomy.

In the above description, numerous specific details are set forth in order to provide a thorough understanding of the present invention. It will be apparent to one skilled in the art, however, that the present invention may be practiced without these specific details. In other instances, well-known components, imaging devices, circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a tangible computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while some aspects of the invention may be embodied in computer software, the functions necessary to implement the invention may alternatively be embodied in part or in whole using hardware components such as application-specific integrated circuits or other hardware, or some combination of hardware components and software.

The invention claimed is:

1. A system to produce images of anatomical structures, the system is adapted for receiving images captured by a catheter having a distal tip furnished with an imaging device capable of capturing images from within a patient's body and a position sensor capable of providing position data indicative of a position of the imaging device; the system comprises one or more processors adapted to carry out the following:

obtaining at least one image captured by the imaging device and the position data indicative of the position of the imaging device within the patient's body when the at least one image is acquired;

utilizing the position data to determine a region captured by the at least one image relative to the patient's body and determining at least a portion of a body anatomy of interest present in the captured region;

providing a model of the body anatomy; and cropping the at least one of image based on the model whereby the cropping comprises utilizing the model to determine association between voxels or pixels of the image and the at least portion of the body anatomy, and removing or blanking the voxels or pixels of the at least one of image which are not associated with the at least portion of the body anatomy to yield at least one cropped image of the body anatomy from which pixels or voxels not associated with the body anatomy are removed or diminished, wherein the cropping is performed based on a registration of the captured region relative to the patient's body as determined from the position data.

2. The system according to claim 1, wherein at least one of the following:

the imaging device comprises an ultrasound imaging device; and the imaging device is adapted for capturing volumetric images from within the patient's body; and the at least one image is a volumetric image captured thereby.

3. The system according to claim 1 comprising a user interface adapted to receive input data indicative of at least a portion of the body anatomy to be presented in the cropped image.

4. The system according to claim 1, wherein said model comprises a morphological model indicative of at least one of a shape, size and position of said at least portion of the body anatomy.

5. The system according to claim 4, wherein said morphological model comprises at least one of the following:

a generic model indicative of at least one of a characteristic shape, characteristic size and characteristic position of said at least portion of the body anatomy;

a patient specific model indicative of at least one of a shape, size and position of said at least portion of the body anatomy of the patient's body; and said morphological model comprises data indicative of one or more properties of one or more tissue types present in said at least portion of the body anatomy.

6. The system according to claim 5 wherein said association between said voxels or pixels of said at least one image and said at least portion of the body anatomy is determined based on a combination of one or more of the following:

determining a fit between the positions of different regions of said body anatomy in the model to corresponding voxels of said at least one image; and determining a fit between tissue properties indicated in the model for different regions of said body anatomy, to spectral data of said corresponding voxels.

7. The system according to claim 1, wherein the model comprises a machine learning model trained for recognition of the body anatomy within images in which the body anatomy appears; and the association is determined by employment of the model to recognize the body anatomy within the at least one image.

8. The system according to claim 1, adapted to produce a cropped video of said at least portion of the body anatomy from which pixels/voxels presenting tissues surrounding said at least portion of the body anatomy are blanked or removed; wherein production of said video comprises operating said one or more processors to process a plurality of images obtained during successive time frames to generate therefrom a video sequence comprising a corresponding plurality of cropped images presenting said at least portion of the patient's body anatomy substantially cleared from body tissues not associated therewith.

9. The system according to claim 8, wherein said images are 3D/volumetric images and said wherein said one or more processors are adapted to produce a cropped 3D/volumetric video presenting said at least portion of the body anatomy.

10. A method to produce images of anatomical structures, the method comprises:

obtaining at least one image captured by a catheter having a distal tip furnished with an imaging device capable of capturing images from within a patient's body and a position sensor capable of providing position data indicative of a position of the imaging device;

obtaining position data indicative of the position of the imaging device within the patient's body when the at least one image is captured;

utilizing the position data to determine a region captured by the at least one image relative to the patient's body;

determining at least a portion of a body anatomy of interest present in the captured region;

providing a model of the body anatomy; and cropping the at least one of image based on the model whereby the cropping comprises utilizing the model to determine association between voxels or pixels of the at least one image and the at least portion of the body anatomy, and removing or blanking the voxels or pixels of the at least one of image which are not associated with the at least portion of the body anatomy to yield at least one cropped image of the body anatomy from which pixels or voxels not associated with the body anatomy are removed or diminished, wherein the cropping is performed based on a registration of the captured region relative to the patient's body as determined from the position data.

11. The method according to claim 10, wherein at least one of the following:

the imaging device comprises an ultrasound imaging device; and the imaging device is adapted for capturing volumetric images from within the patient's body; and the at least one image is a volumetric image captured thereby.

12. The method according to claim 10 comprising receiving, from a user interface, input data indicative of the at least portion of the body anatomy to be presented in the cropped image.

13. The method according to claim 10, wherein said model comprises a morphological model indicative of at least one of a shape, size and position of said at least portion of the body anatomy.

14. The method according to claim 13, wherein said morphological model comprises at least one of the following:

a generic model indicative of at least one of a characteristic shape, characteristic size and characteristic position of said at least portion of the body anatomy;

a patient specific model indicative of at least one of a shape, size and position of said at least portion of the body anatomy of the patient's body; and said morphological model comprises data indicative of one or more properties of one or more tissue types present in said at least portion of the body anatomy.

15. The method according to claim 14 wherein said association between said voxels or pixels of said at least one image and said at least portion of the body anatomy is determined based on a combination of one or more of the following:

determining a fit between the positions of different regions of said body anatomy in the model to corresponding voxels of said at least one image; and determining a fit between tissue properties indicated in the model for different regions of said body anatomy, to spectral data of said corresponding voxels.

16. The method according to claim 10, wherein the model comprises a machine learning model trained for recognition of the body anatomy within images in which the body anatomy appears; and the association is determined by employment of the model to recognize the body anatomy within the at least one image.

17. The method according to claim 10, comprising producing a cropped video of said at least portion of the body anatomy from which pixels/voxels presenting tissues surrounding said at least portion of the body anatomy are blanked or removed; wherein production of said video comprises processing a plurality of images captured during successive time frames by said imaging device to generate therefrom a video sequence comprising a corresponding plurality of cropped images presenting said at least portion of the patient's body anatomy substantially cleared from body tissues not associated therewith.

18. The method according to claim 17, wherein said images are 3D/volumetric images and said wherein the method is adapted to produce said cropped video as a 3D/volumetric video presenting said at least portion of the body anatomy.

19. The system according to claim 1, wherein the one or more processors are further adapted to determine the region captured by the at least one image based on the position data and one or more capturing parameters of the imaging device.

20. The method according to claim 10, wherein determining the region captured by the at least one image comprises determining the region captured by the at least one image based on the position data and one or more capturing parameters of the imaging device.

21. The system according to claim 1, wherein the one or more processors are adapted to automatically determine the at least portion of the body anatomy of interest based on the position data and a knowledgebase indicative of locations of anatomical structures within patients' bodies.

22. The method according to claim 10, wherein determining the at least portion of the body anatomy of interest comprises automatically determining the at least portion of the body anatomy based on the position data and a knowledgebase indicative of locations of anatomical structures within patients' bodies.

23. The system according to claim 3, wherein the user interface is adapted to present an initial image captured by the imaging device and receive a user selection of the at least portion of the body anatomy from the presented initial image.

24. The method according to claim 12, further comprising presenting an initial image captured by the imaging device via the user interface and receiving a user selection of the at least portion of the body anatomy from the presented initial image.

* * * * *